US006977987B2

(12) United States Patent
Yamashita et al.

(10) Patent No.: US 6,977,987 B2
(45) Date of Patent: Dec. 20, 2005

(54) RADIOTHERAPY APPARATUS

(75) Inventors: Ichiro Yamashita, Hiroshima-ken (JP);
Yuichiro Kamino, Aichi-ken (JP); Ikuo Wakamoto, Hiroshima-ken (JP);
Kazumasa Mihara, Hiroshima-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 42 days.

(21) Appl. No.: 10/762,358

(22) Filed: Jan. 23, 2004

(65) Prior Publication Data

US 2004/0174949 A1    Sep. 9, 2004

Related U.S. Application Data

(63) Continuation of application No. PCT/JP02/08505, filed on Aug. 23, 2002.

(51) Int. Cl.$^7$ ................................................ A61N 5/10
(52) U.S. Cl. ....................................... 378/64; 378/65
(58) Field of Search ........................... 315/5.41, 500, 315/505; 378/64, 65; 600/411, 422

(56) References Cited

U.S. PATENT DOCUMENTS

| | | | |
|---|---|---|---|
| 3,466,439 A | 9/1969 | Edvard | 378/65 |
| 4,230,129 A | 10/1980 | LeVeen | 607/154 |
| 6,060,833 A * | 5/2000 | Velazco | 315/5.41 |
| 6,118,847 A * | 9/2000 | Hernandez-Guerra et al. | 378/65 |
| 6,307,914 B1 | 10/2001 | Kunieda et al. | 378/65 |
| 6,366,798 B2 * | 4/2002 | Green | 600/411 |
| 6,385,286 B1 | 5/2002 | Fitchard et al. | 378/65 |

FOREIGN PATENT DOCUMENTS

| | | |
|---|---|---|
| JP | 34-7095 | 8/1959 |
| JP | 52-18073 | 4/1977 |
| JP | 62-206798 | 9/1987 |
| JP | 6-502330 | 3/1994 |
| JP | 8-504347 | 5/1996 |

* cited by examiner

*Primary Examiner*—David Vu
(74) *Attorney, Agent, or Firm*—Armstrong, Kratz, Quintos, Hanson & Brooks, LLP

(57) ABSTRACT

A radiotherapy apparatus comprising an irradiation head having a linear accelerator and an intra-head waveguide unit whose one end portion is electromagnetically connected to the linear accelerator, a supporting moving mechanism which supports and moves the irradiation head on predetermined first spherical coordinates, a microwave oscillator which generates microwaves to be supplied to the irradiation head, and which is placed in a stationary position, a fixed waveguide unit having one end portion electromagnetically connected to the microwave oscillator, and the other end portion positioned on the supporting moving mechanism, and a moving waveguide unit having one end portion electromagnetically connected to the other end portion of the fixed waveguide unit positioned on the supporting moving mechanism.

12 Claims, 30 Drawing Sheets

Irradiation direction of therapeutic radiation

RADIOTHERAPY APPARATUS

CROSS-REFERENCE TO RELATED APPLICATIONS

This is a Continuation Application of PCT Application No. PCT/JP02/08505, filed Aug. 23, 2002, which was not published under PCT Article 21(2) in English.

This application is based upon and claims the benefit of priority from the prior Japanese Patent Applications No. 2001-254891, filed Aug. 24, 2001; and No. 2001-254892, filed Aug. 24, 2001, the entire contents of both of which are incorporated herein by reference.

BACKGROUND OF THE INVENTION

1. Field of the Invention

The present invention relates to a radiotherapy apparatus suited to performing, e.g., radiotherapy on a tumor by a stereotactic pluridirectional irradiation method.

2. Description of the Related Art

A stereotactic pluridirectional irradiation method is one radiotherapy method capable of increasing the therapeutic effect by intensively irradiating a diseased part with radiation in multiple directions, and minimizing the exposure dose of the surrounding tissue of the diseased part.

This stereotactic pluridirectional irradiation method is considered effective in curing diseased parts, such as a primary benign brain tumor, a simple metastatic brain tumor having a size of 3 cm or less, a small morbid part in the brain, e.g., skull base metastasis which is difficult to operate, arterial malformation, and venous malformation.

As a radiotherapy apparatus capable of practicing this stereotactic pluridirectional irradiation method, an apparatus which performs irradiation after positioning an irradiation head with respect to a patient by using a positioning means is conventionally known. Since, however, a doctor or assistant does not confirm the position of a focus by directly viewing the irradiation field before irradiation, the accuracy of irradiation is not high.

International Patent Laid-Open Nos. 6-502330 and 8-504347 disclose a system which combines a radiotherapy apparatus with an X-ray CT apparatus by incorporating a linear accelerator into a rotary drum of the X-ray CT apparatus. In this system, irradiation can be performed while confirming an image of the irradiation field.

Unfortunately, these apparatuses have a structure in which the linear accelerator is incorporated into the rotary drum of the X-ray CT apparatus. Therefore, irradiation can be performed only around one rotational axis, thus this irradiation is limited to isocentric irradiation.

BRIEF SUMMARY OF THE INVENTION

It is an object of the present invention to provide a radiotherapy apparatus having a high therapeutic performance.

To achieve the above object, the present invention is a radiotherapy apparatus comprising:

an irradiation head having a linear accelerator and an intra-head waveguide unit whose one end portion is electromagnetically connected to the linear accelerator;

a supporting moving mechanism which supports and moves the irradiation head on predetermined first spherical coordinates;

a microwave oscillator which generates microwaves to be supplied to the irradiation head, and which is placed in a stationary position;

a fixed waveguide unit having one end portion electromagnetically connected to the microwave oscillator, and the other end portion positioned on the supporting moving mechanism; and a moving waveguide unit having one end portion electromagnetically connected to the other end portion of the fixed waveguide unit positioned on the supporting moving mechanism, and the other end portion electromagnetically connected to the other end portion of the intra-head waveguide unit.

BRIEF DESCRIPTION OF THE SEVERAL VIEWS OF THE DRAWING

FIGS. 13A, 13B, and 13C illustrate an irradiation head of the radiotherapy apparatus according to the same embodiment of the present invention, in which FIG. 13B is a sectional view taken along a line XIIIB—XIIIB in FIG. 13A, and FIG. 13C is a sectional view taken along a line XIIIC—XIIIC in FIG. 13A;

FIGS. 20A to 20D illustrate head rotating mechanisms of the same embodiment, in which FIG. 20A is a perspective view showing waveguides, the head rotating mechanisms, and driving motors, FIG. 20B is a sectional view taken along a line XXB—XXB in FIG. 20A, FIG. 20C is a sectional view taken along a line XXC—XXC in FIG. 20A, and FIG. 20D is a sectional view taken along a line XXD—XXD in FIG. 20A;

FIGS. 35A and 35B illustrate the irradiation head of the same embodiment, in which FIG. 35A is a front view and FIG. 35B is a side view;

DETAILED DESCRIPTION OF THE INVENTION (First Embodiment)

Figure 1:
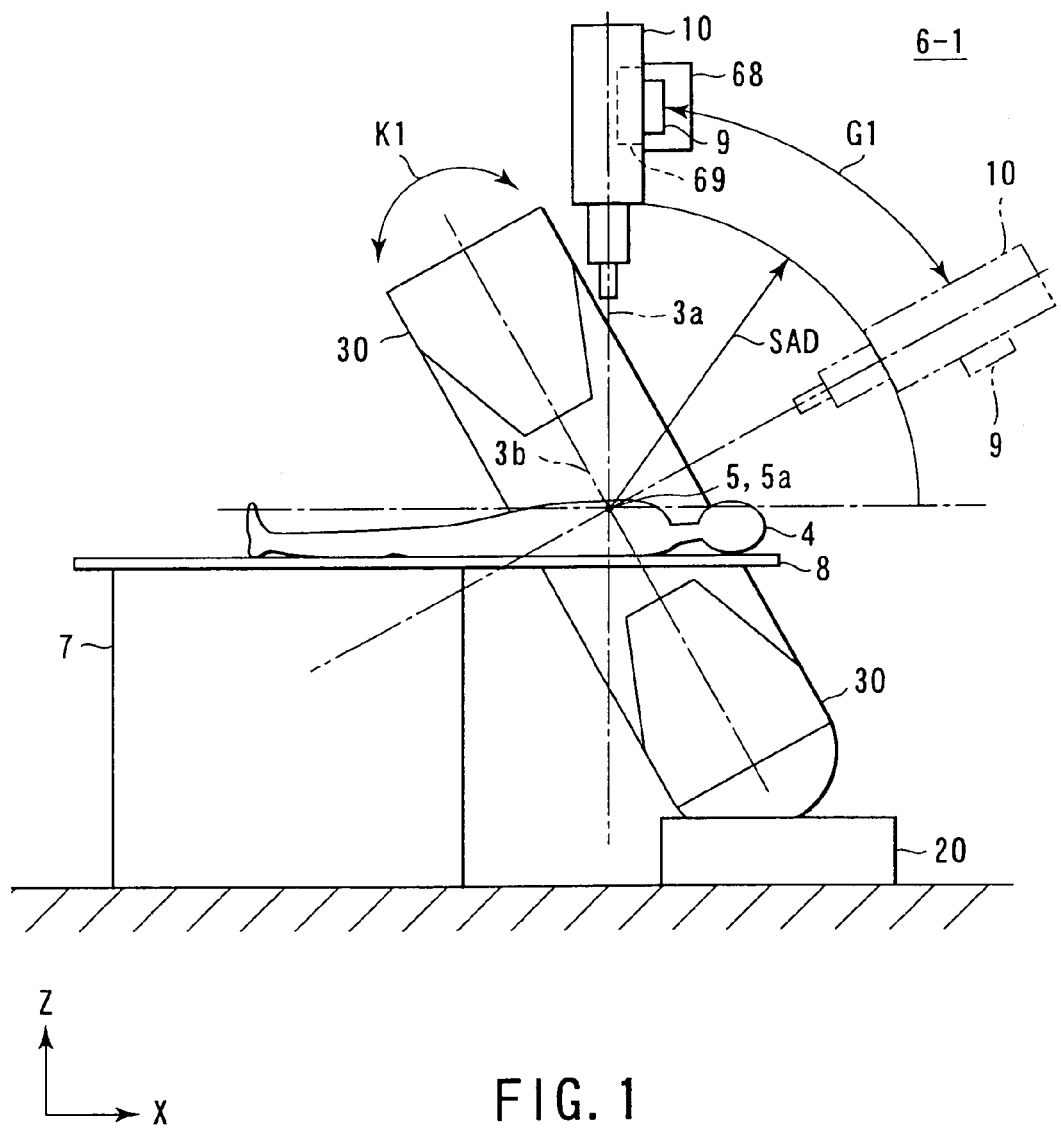
FIG. 1 is a view showing a radiotherapy apparatus according to the first embodiment of the present invention in a direction perpendicular to the bed axis.
Figure 2:
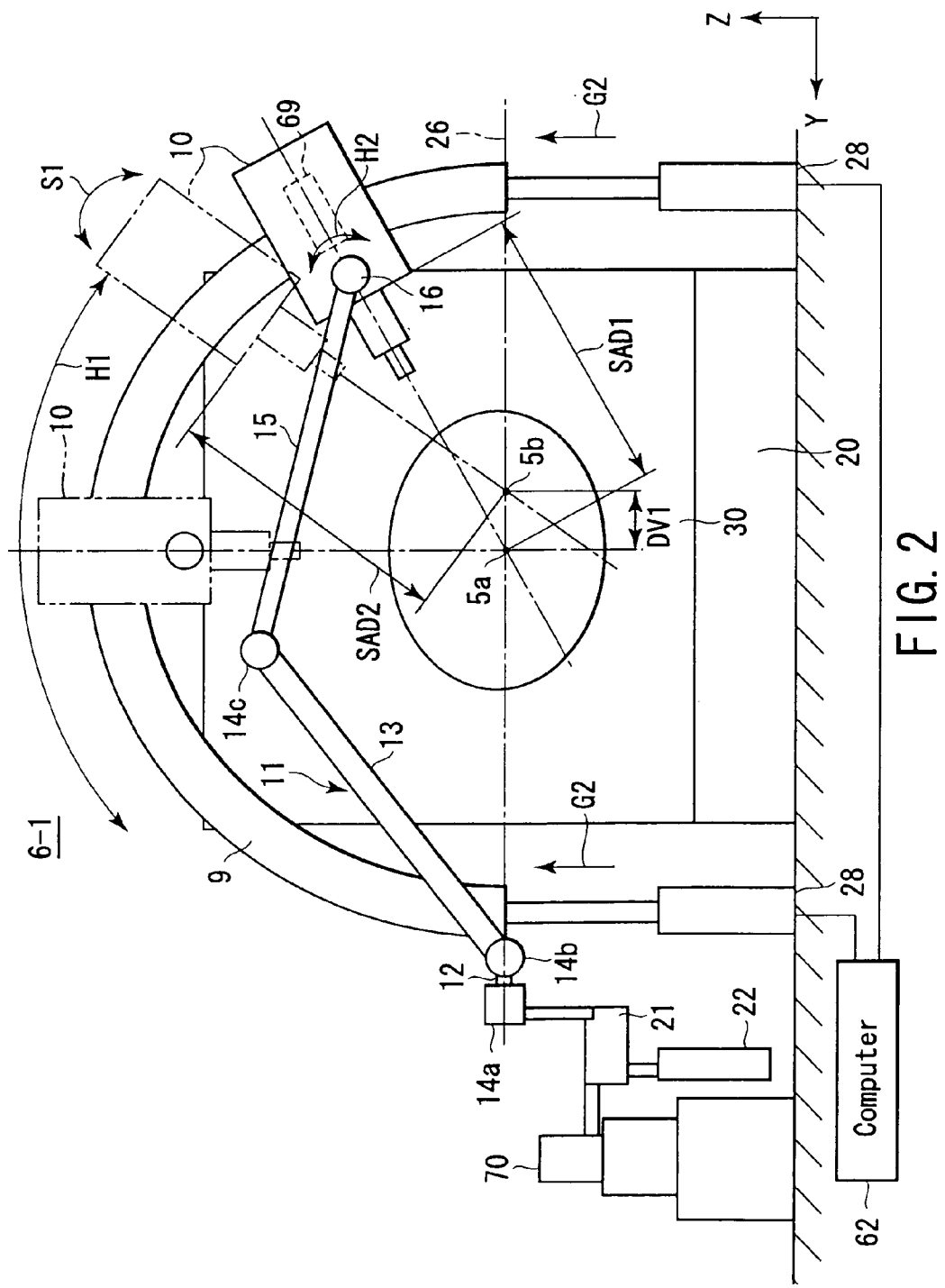
FIG. 2 is a view showing the radiotherapy apparatus of the same embodiment in the bed axis direction.
Figure 3:
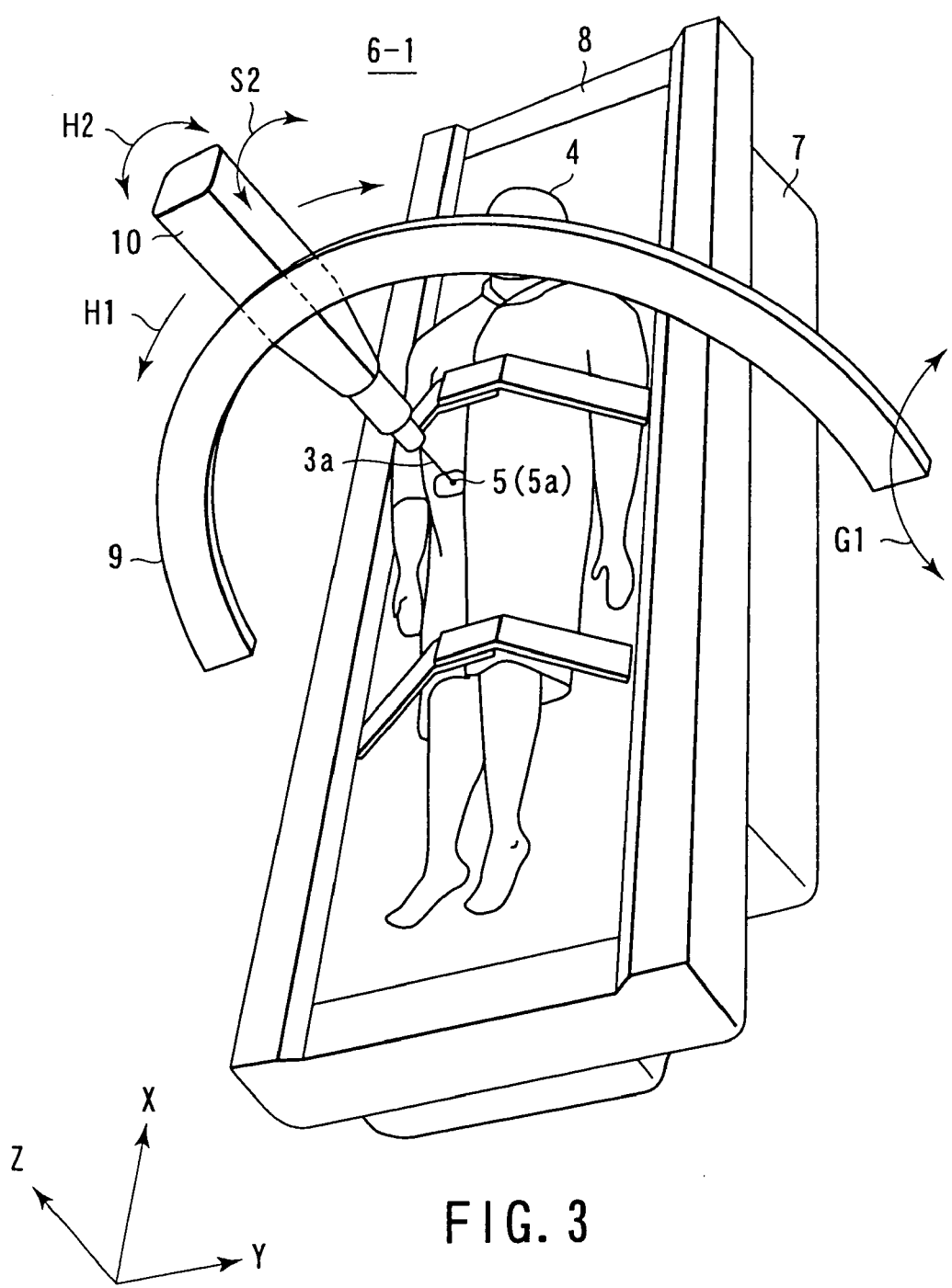
FIG. 3 is a perspective view for explaining radiotherapy performed by the radiotherapy apparatus of the same embodiment.

As shown in FIGS. 1 to 3, a radiotherapy apparatus 6-1 according to this embodiment includes a bed 7 having a top plate 8 on which a patient 4 is placed, an irradiation head 10 for irradiating an irradiation field 5 settable in the patient 4 with therapeutic radiation, and an X-ray CT apparatus 30 for acquiring a tomographic image of the irradiation field 5 as a diseased part.

Referring to FIG. 1, the top plate 8 can be moved in three axis directions, i.e., a bed longitudinal direction (X-axis direction), bed widthwise direction (Y-axis direction), and bed vertical direction (Z-axis direction), by an X-Y driving mechanism (not shown) contained in the bed 7. Also, the position of this top plate 8 is controlled by a computer system (not shown) on the basis of an image taken by a TV camera (not shown), so that the irradiation field 5 of the patient 4 is positioned in an isocenter 5a. Furthermore, the material and shape of the top plate 8 are so selected as to match the X-ray CT apparatus 30 as an image acquiring apparatus or a PET (Positron Emission Tomography) apparatus. Reference numeral 3b denotes image acquiring X-rays (image acquiring radiation) of the X-ray CT apparatus 30; and 20, an inclining mechanism for inclining the X-ray CT apparatus 30 in a direction K1 shown in FIG. 1.

The patient 4 is placed on the top plate 8 such that his or her body axis lies along the bed longitudinal direction. The X- and Y-axis directions are horizontal directions, and the Z-axis direction is a vertical direction.

The irradiation head 10 is movably supported by a substantially semicircular arch-shaped guide rail 9 via a circumferential moving mechanism 68 and head rotating mechanism 69, and emits therapeutic radiation 3a. This irradiation head 10 is positioned in an arbitrary irradiation position within the range of a half sphere around the isocenter 5a by the circumferential moving mechanism 68 and head rotating mechanism 69.

As shown in FIG. 2, the circumferential moving mechanism 68 circumferentially moves (H1) the irradiation head 10 along the guide rail 9. A rack and pinion or belt can be used. The irradiation head 10 is also coupled with a fourth joint 16 of waveguide systems 11 and 15. The irradiation head 10 is, as shown in detail in FIG. 4 (to be described later), the irradiation head 10 is electromagnetically connected to a microwave oscillator 70 such as a klystron via waveguides 50, 51, and 52 forming the waveguide system 11. As shown in FIG. 2, the head rotating mechanism 69 rotates (H2) the irradiation head 10 on the guide rail 9 around the fourth joint 16. The irradiation head 10 has a total length of 800 to 1,000 mm and an outer dimension of 300 to 500 mm.

As shown in FIGS. 2 and 3, the guide rail 9 is a semicircular ring which forms the upper half of a circle above the top plate 8, and is formed across this top plate 8 in the widthwise direction. This guide rail 9 is movably supported by a tilting mechanism and a pair of cylinder mechanisms 28. The tilting mechanism tilts (G1) the guide rail 9 around a tilting axis 26 shown in FIG. 2 within the range of 0° to 180°, as shown in FIG. 1. The guide rail 9 is made of a very rigid material such as stainless steel, and has a width of 200 to 400 mm, a thickness of 20 to 50 mm, and a radius of 800 to 1,000 mm from the isocenter 5a.

As shown in FIG. 2, the pair of cylinder mechanisms 28 support the left and right lower end portions of the guide rail 9, and move this guide rail 9 up and down (G2) in the Z-axis direction. These cylinder mechanisms 28 are controlled by a computer 62 as a position control means, such that their operations are synchronized.

In this embodiment as described above, the tilt (G1) of the guide rail 9 and the circumferential motion (H1) of the irradiation head 10 allow isocentric motion of the irradiation head 10 on a half sphere around the isocenter 5a. Also, the vertical motion (G2) of the guide rail 9 and the rotation (H2) of the irradiation head 10 allow non-isocentric motion of the irradiation head 10 in a position deviated from the half sphere around the isocenter 5a.

The X-ray CT apparatus 30 has a donut-like vacuum bath, and contains a large number of concentrically arranged X-ray generating units in this vacuum bath. The vacuum bath has a central opening, and this opening is used as a diagnostic space. That is, the patient 4 and the top plate 8 are taken in and out through this diagnostic space.

The X-ray CT apparatus 30 of this embodiment is a nonmagnetic image acquiring apparatus. The X-ray CT apparatus 30 of this embodiment is a so-called fifth-generation apparatus in which an X-ray source and detector remain stationary, and this will be explained in more detail later. Instead of this X-ray CT apparatus 30 of this embodiment, it is also possible to use a third-generation X-ray CT apparatus in which an X-ray source and detector rotate, or a fourth-generation X-ray CT apparatus in which an X-ray source rotates and a detector remains stationary.

The X-ray CT apparatus 30 of this embodiment can be supported as it is inclined through, e.g., 200 to 30° to the Z axis by the image acquiring apparatus inclining mechanism 20 shown in FIG. 1. When this inclining mechanism 20 is driven, the X-ray CT apparatus 30 tilts (K1) to change the irradiation angle of the image acquiring X-ray 3b. The X-ray CT apparatus 30 and guide rail 9 are mechanically closely connected, and have a common coordinate reference. The X-ray CT apparatus 30 is so controlled that the guide rail 9 and irradiation head 10 do not interfere with each other. When an X-ray fluoroscopic apparatus is used in place of the X-ray CT apparatus 30 as an image acquiring apparatus, the resolution and contrast are lower than those of the X-ray CT apparatus 30. Therefore, a small gold plate, for example, is embedded near the irradiation field, and an image of this gold plate is taken into a fluoroscopic image. In this manner, high positional accuracy can be assured by using the plate image as a marker and marking the irradiation field on the basis of this marker.

As an image acquiring apparatus, PET can also be used instead of the X-ray CT apparatus or X-ray fluoroscopic apparatus described above. In addition, an MRI apparatus can also be used as a magnetic image acquiring apparatus.

SAD (Source Axis Distance) shown in FIG. 1 is the distance from the isocenter 5a to a target 110 (FIG. 4) in the irradiation head 10. In this embodiment, this SAD is set at 80 cm.

In this embodiment, as shown in FIG. 2, the computer 62 performs positioning calculations using a shift amount DV1 from the isocenter 5a to a non-isocenter 5b by $$H1 = \theta 1 \quad (1)$$

$$H2 = \theta 1 - \arctan((r \sin \theta 1 - DV1)/(r \cos \theta 1)) \quad (2)$$

$$G1 = 0 \quad (3)$$

$$G2 = z \quad (4)$$

where
  θ1: the rotational angle the guide rail 9 makes with the isocenter vertical axis
  r: the radius of curvature of the guide rain 9
  z: a vertical deviation from the isocenter 5a In accordance with the calculation results, the computer 62 controls driving (G1 and G2) of the guide rail 9 and driving (H1 and H2) of the irradiation head 10 when the non-isocenter 5b is irradiated with X-rays.

Referring to FIG. 2, joints 14a to 14c and the joint 16 of the waveguide system 11 contain a rotary RF coupler 50 for transmitting accelerating microwaves by axial rotation.

Figure 5:
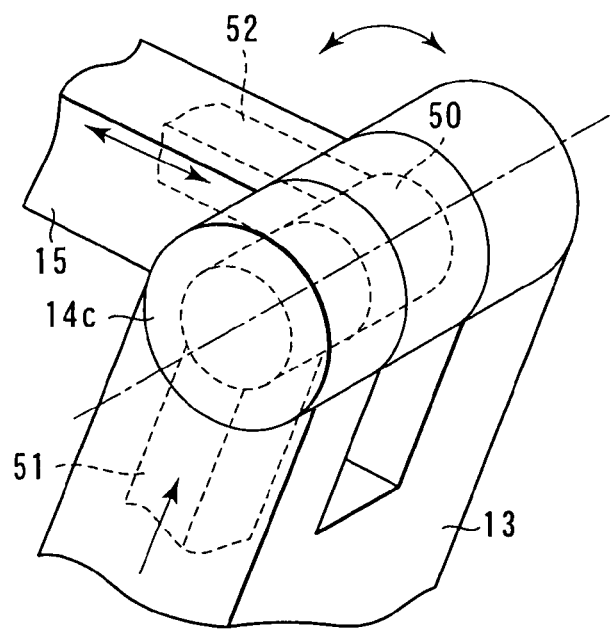
FIG. 5 is a perspective view showing a waveguide system and rotary RF coupler of the radiotherapy apparatus of the same embodiment.

Also, as shown in FIG. 5, the waveguides 51 and 52 are formed in the waveguide system 11. These waveguides 51 and 52 electromagnetically communicate with each other by the rotary RF coupler 50 in the joints 14a to 14c.

Figure 6:
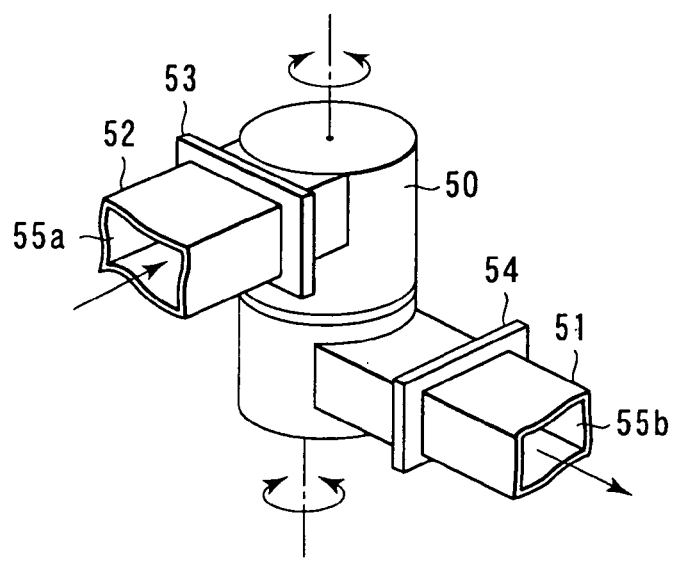
FIG. 6 is a perspective view showing the rotary RF coupler and waveguides of the radiotherapy apparatus of the same embodiment.

Furthermore, as shown in FIG. 6, the rotary RF coupler 50 is connected to the waveguides 51 and 52 by flange couplings 53 and 54, respectively. Reference numerals 55a and 55b denote waveguides of these waveguides 51 and 52.

Figure 7:
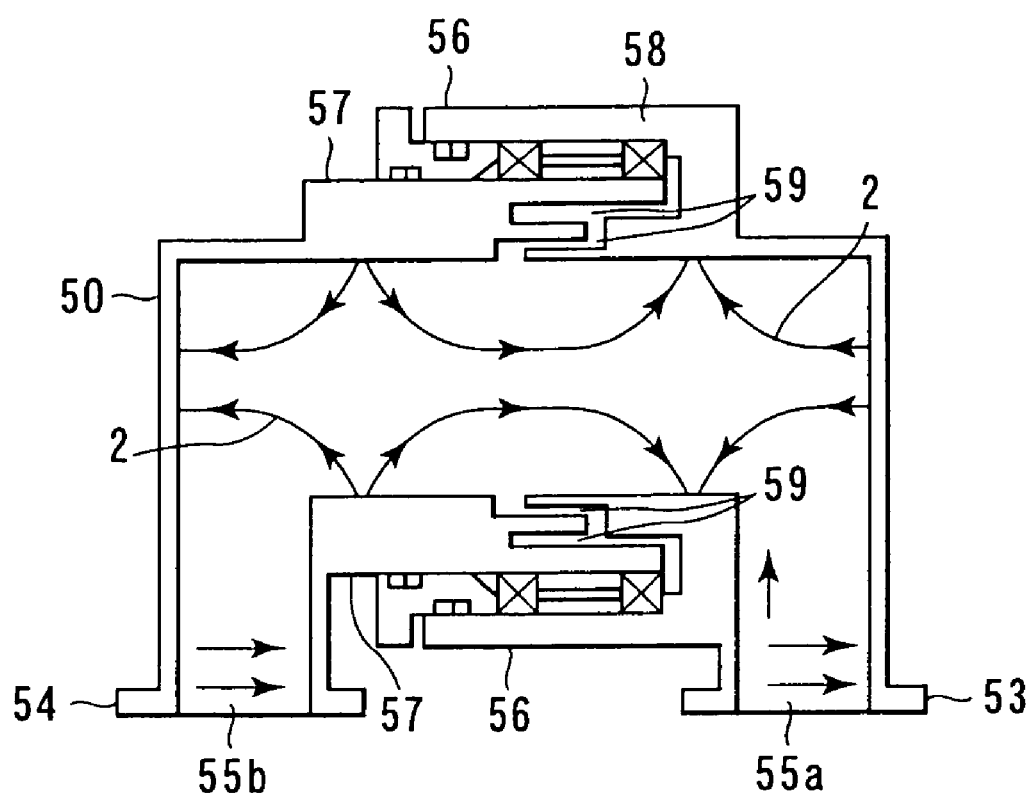
FIG. 7 is a view for explaining the rotary RF coupler of the radiotherapy apparatus of the same embodiment.

In addition, as shown in FIG. 7, these waveguides 55a and 55b of the waveguides 51 and 52 communicate with a rotating space surrounded by rotating members 56 and 57 of the rotary RF coupler 50. Therefore, an electric field (vector or mode) is formed in this rotating space, and microwaves propagate. In FIG. 7, reference numeral 58 denotes a bearing; and 59, a λ/4-wave choke. By the combination of the rotary RF coupler 50 and waveguides 51 and 52 as described above, accelerating microwaves can be smoothly supplied from the microwave oscillator, such as a klystron, fixed on the floor or the like, to the moving irradiation head 10.

As shown in FIG. 2, the waveguide system 11 is a link mechanism having one end fixed to the end portion of the guide rail 9 via the first joint 14a, and the other end connected to the irradiation head 10 via the fourth joint 16. Reference numeral 21 denotes a circulator; and 22, a dummy load.

The waveguide system 11 is made up of the first joint 14a fixed to the end portion of the guide rail 9, a first waveguide 12 having one end rotatably connected to the first joint 14a, the second joint 14b to which the other end of the first waveguide 12 is connected, a second waveguide 13 having one end connected to the second joint 14b, the third joint 14c to which the other end of the second waveguide 13 is connected, a third waveguide 15 having one end connected to the third joint 14c, and the fourth joint 16 to which the other end of the third waveguide 15 is connected, and which is connected to the irradiation head 10.

Only the first joint 14a is formed along the Y axis, and the second to fourth joints 14b, 14c, and 16 are formed along the X axis.

The X-ray CT apparatus 30 will be described in detail below.

This X-ray CT apparatus 30 irradiates the irradiation field 5 of an object to be examined such as the patient 4 with the image acquiring X-rays 3b as fan-shaped X-rays in multiple directions, detects transmitted X-rays, and performs image processing for the detection data, thereby displaying a tomographic image of the irradiation field 5 on the computer screen.

The X-ray CT apparatus 30 of this embodiment is a so-called fifth-generation apparatus including a donut-like vacuum bath (not shown) having a central opening as a diagnostic space. This vacuum bath is evacuated by a vacuum pump through an exhaust port. The vacuum bath contains a large number of X-ray generating units (not shown) arranged on the same circle near the outer circumference, and a large number of sensor arrays (not shown) arranged on the same circle near the inner circumference in one-to-one correspondence with the large number of X-ray generating units. These X-ray generating units and sensor arrays are shifted in the X-axis direction, so the image acquiring X-rays 3b are emitted in the form of a fan in a direction in which the X-rays 3b incline forward with respect to the radius of the vacuum bath. Accordingly, the fan-shaped image acquiring X-rays 3b are transmitted through the patient 4 in the diagnostic space without being interrupted by the sensor array on the X-ray irradiation side, and the transmitted X-rays can be detected by the sensor array on the opposite side.

In addition, a beam limiter, electron gun driving circuit, image signal digitizer, and the like are arranged in the vacuum bath. The fan-shaped X-rays 3b emitted from the X-ray generating units are collimated by a collimator, and limited to the width at the irradiation position by the beam limiter.

The sensor arrays are densely fixed on the circumference surrounding the diagnostic space, include a large number of ultra high sensitivity CdTe sensors, and have a resolution of 0.5 mm. The image sensing width of one shot during image acquisition is approximately 80 mm. Also, the X-ray irradiation time is 0.01 sec for one shot.

An X-ray generation controller (not shown) is connected to a data recorder (not shown), and receives an X-ray generation command signal from the computer 62. X-ray transmission data detected by the sensor arrays is converted into an electric current signal proportional to the transmitted X-ray amount, supplied to the digitizer (not shown) and the data recorder (not shown) via a preamplifier and main amplifier (neither is shown), and recorded. The data recording timing is controlled by the X-ray generation command signal from the computer 62. The recorded data is output from the data recorder to a signal processor (not shown), and processed by this signal processor. The processed data is displayed as a tomographic image of the irradiation field 5 on a display (not shown).

The output terminal of the X-ray generation controller is connected to a power supply and anodes, cathodes, and gate array grid electrodes (none of them are shown) in the X-ray generating units. When the X-ray generation command signal is output from the computer 62 to this X-ray generation controller, the X-ray generation controller controls the supply of power from the power supply (not shown) to the electron gun driving circuit (not shown), and selects a grid electrode suited to an image sensing portion from the gate array, on the basis of the command. In response to this, an electron beam is emitted from a certain cathode in the X-ray generating units, a minus bias voltage applied to the selected grid electrode is released to zero potential, and the electron beam enters the anode through a hole in the grid electrode. When the electron beam thus enters the anode, the anode generates secondary X-rays, so the fan-shaped image acquiring X-rays 3b are emitted toward the patient 4 through the collimator attached to the window.

When the transmitted X-ray data of the irradiation field 5 is input from the X-ray CT apparatus 30, the computer 62 controls the driving of the circumferential moving mechanism 68, head rotating mechanism 69, and inclining mechanism 20 on the basis of the data, thereby finely adjusting the position and direction of the irradiation head 10 to allow this irradiation head 10 to aim at the irradiation field 5 in the isocenter 5a or non-isocenter 5b.

Figure 4:
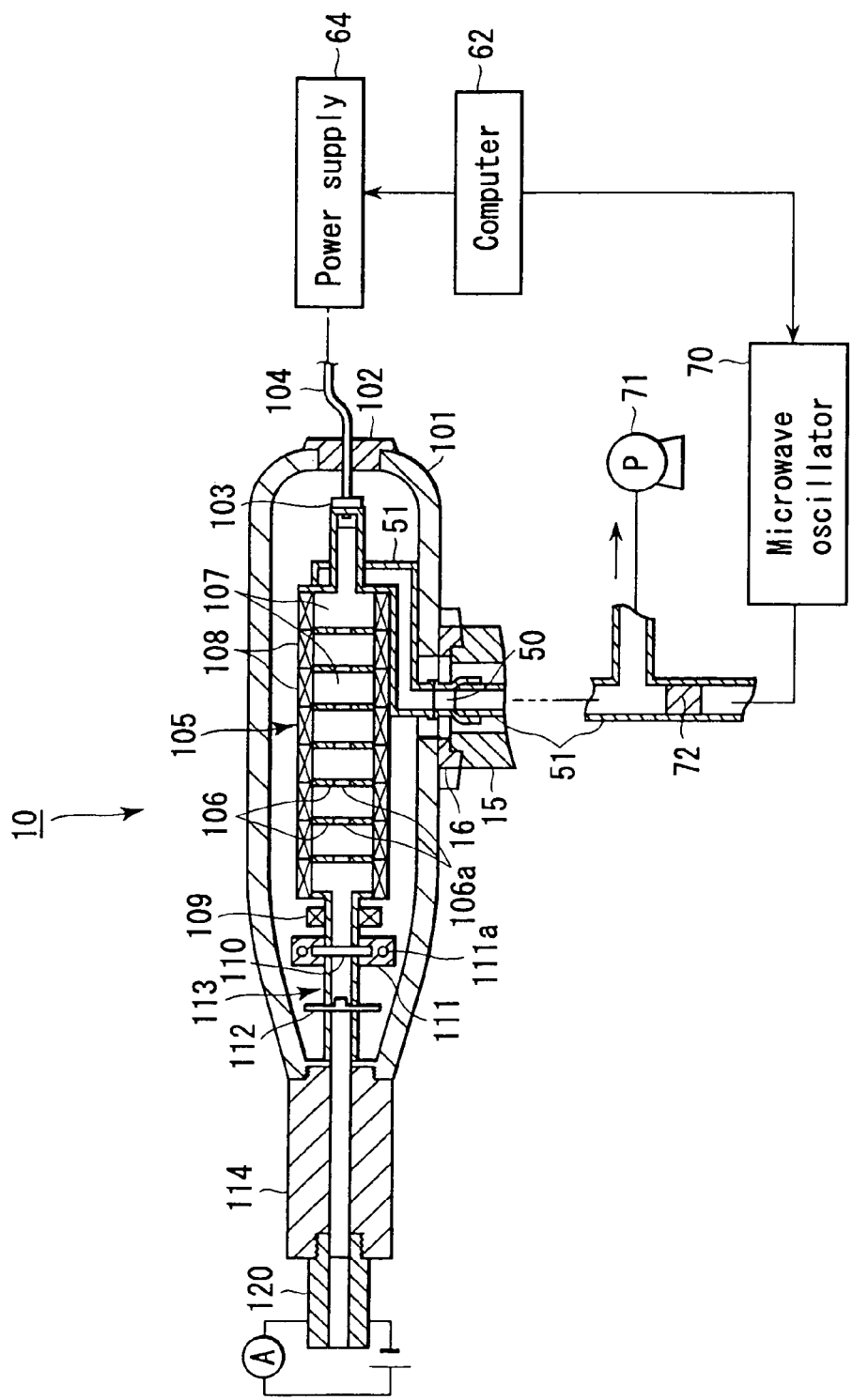
FIG. 4 is a partial sectional view of an irradiation head of the radiotherapy apparatus of the same embodiment.

Details of the irradiation head 10 will be described below with reference to FIG. 4.

The irradiation head 10 of this embodiment generates therapeutic radiation 3a by accelerating electrons to an energy of 4 to 20 MeV, and functions as a subminature electron linac irradiation head. The outside of this irradiation head 10 is covered with an outer case 101 which shields radiation. Inside this outer case 101, the irradiation head 10 has an electron gun 103, an accelerator 105, a focusing coil 109, the X-ray target 110, a flattening filter 112, and a focusing tube 113.

The rear end of the outer case 101 is covered with an insulating cap 102. A cable 104 connected to a power supply 64 is introduced into the case 101 via this insulating cap 102, and connected to the electron gun 103. The output from the power supply 64 of the electron gun 103 is controlled by the computer 62.

Components from the electron gun 103 to the flattening filter 112 are arranged in series along the central axis of an electron beam. The accelerator 105 follows the electron gun 103, and the focusing tube 113 follows the accelerator 105.

The waveguide 51 communicates with the accelerator 105. This waveguide 51 also communicates with the microwave oscillator 70 and a vacuum pump 71. Therefore, the accelerator 105 is evacuated by the pump 71 through the waveguide 51. A ceramic window 72 is fitted in the main path of the waveguide 51, that branches and communicates with the vacuum pump 71. This ceramic window 72 prevents leakage of $SF_6$ gas sealed in a waveguide from the microwave oscillator 70 to the ceramic window 72, and passes only microwaves.

The microwave oscillator 70 is a klystron type oscillator superior in output stability. A power supply circuit of this microwave oscillator 70 is connected to the computer 62. The electron gun 103 has a filament (cathode) formed in a chamber evacuated by the vacuum pump 71.

The accelerator 105 follows and communicates with the chamber in which the electron gum 103 is accommodated, and accelerates an output electron beam from this electron gun 103. The interior of this accelerator 105 is divided by a plurality of partitions 106 to form a plurality of acceleration chambers 107. An electron beam passing hole 106a is formed in the center of the partition 106. A coil 108 is wound around the outer surface of each acceleration chamber 107, and connected to a power supply circuit whose operation is controlled by the computer 62.

The focusing tube 113 follows the accelerator 105. To this focusing tube 113, the focusing coil 109, X-ray target 110, and flattening coil 112 are attached in this order. The focusing coil 109 focuses the electrons accelerated by the accelerator 105 toward the X-ray target 110.

The X-ray target 110 receives high-energy accelerated electrons and outputs bremsstrahlung X-rays. Therefore, a water cooling jacket 111 having a flow path 111a is attached to this X-ray target 110 to forcedly cool it in order to prevent thermal damage. As this target 110, it is preferable to use a metal such as tungsten, molybdenum, or tantalum, or an alloy of any of these metals.

The flattening filter 112 is made of a metal, and forms the therapeutic radiation 3a having a substantially uniform energy density by averaging the intensities of X-rays emitted from the target 110.

Furthermore, a collimator 114 and dose measurement tube 120 are attached to the outside of the outer case 101. The collimator 114 is screwed into the distal end of the outer case 101, and has a hollow portion which communicates with the focusing tube 113. This collimator 114 is made of a highly shielding material, such as lead, through which the therapeutic radiation 3a cannot pass. The X-rays 3a are supplied to the dose measurement tube 120 through the hollow portion.

The dose measurement tube 120 is an ionization chamber in which a gas is sealed. This dose measurement tube 120 detects the charge amount of ionized gas generated when radiation passes by, and measures the dose of the radiation.

Figure 8:
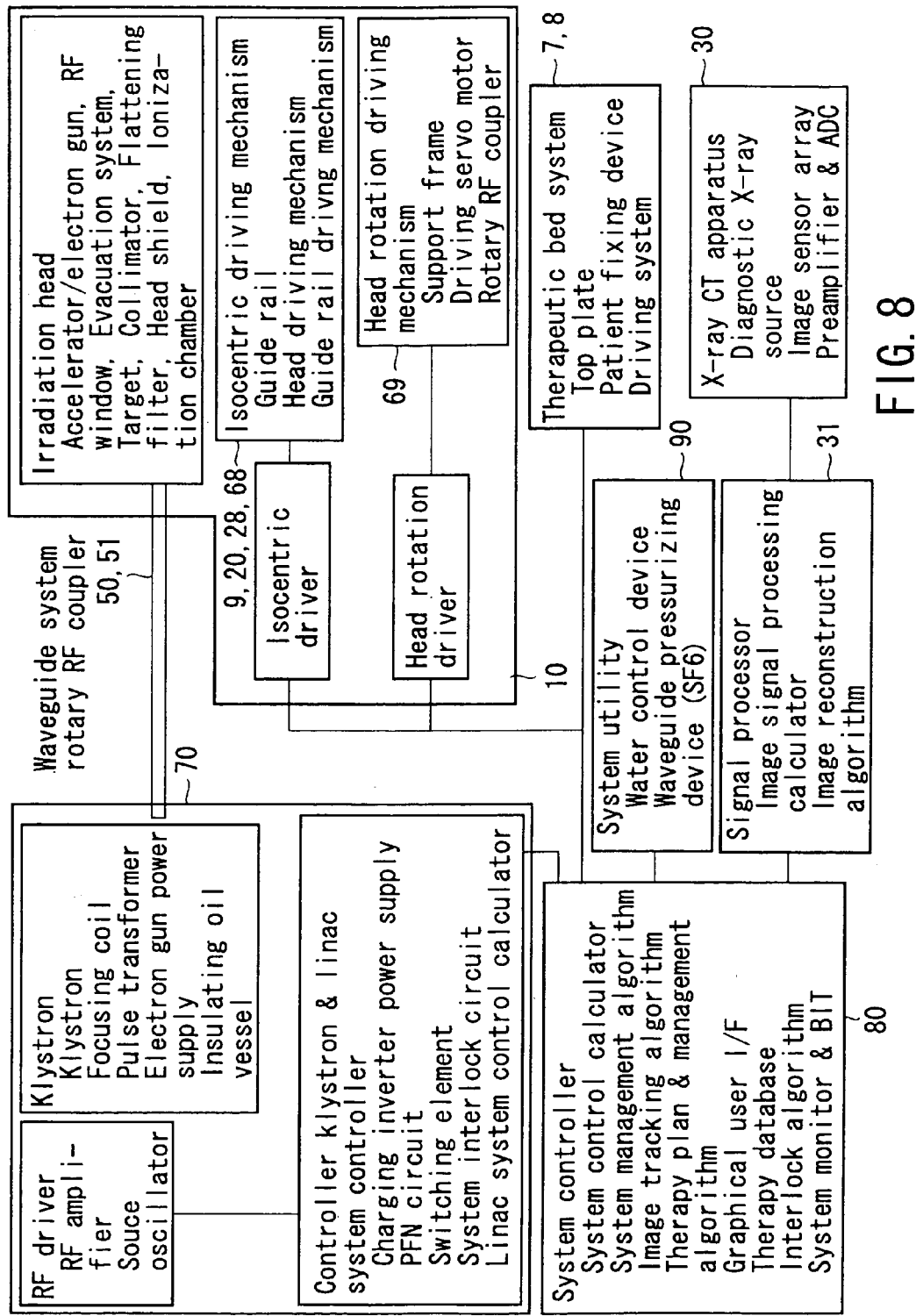
FIG. 8 is a block diagram of the radiotherapy apparatus of the same embodiment.

A control system of the apparatus of this embodiment will be described below with reference to FIG. 8.

The radiotherapy apparatus of this embodiment has a control system including the therapeutic bed system 7 and 8, the irradiation head 10, the X-ray CT apparatus 30, a signal processor 31, the microwave oscillator 70, a system controller 80, and a system utility 90. The system controller 80 controls the whole system.

This system controller 80 includes a system control calculator, system management algorithm, image tracking algorithm, therapy plan algorithm, therapy management algorithm, graphical user interface, therapy database, interlock algorithm, and system monitor. The system controller 80 comprehensively controls the entire control system, and exchanges input and output signals with other blocks.

The X-ray CT apparatus 30 is connected to the system controller 80 via the signal processor 31. During radiotherapy, therefore, the X-ray CT apparatus 30 acquires images in real time, so a doctor can perform the therapy while monitoring the images on the display.

The microwave oscillator 70 comprises a klystron modulator and linac system controller, a klystron, and an RF driver. The klystron as a source for supplying microwaves to the accelerator 110 is connected to the irradiation head 10 via the waveguide system 11.

The isocentric driving mechanism and head rotating mechanism of the irradiation head 10 are connected to the system controller 80 to control circumferential motion driving of the irradiation head 10 during isocentric irradiation and biaxial head rotation driving of the irradiation head 10 during pseudo non-isocentric irradiation.

A therapeutic method using the apparatus of the present invention will be explained below with reference to FIG. 9.

In radiotherapy, a doctor makes a therapy plan. This therapy plan is based on various examinations performed before the operation. In addition, during the operation, the doctor directly acquires images of a diseased part in real time by using the radiotherapy apparatus of this embodiment. By this image acquisition, high-accuracy, high-reliability radiotherapy can be performed.

Figure 9:
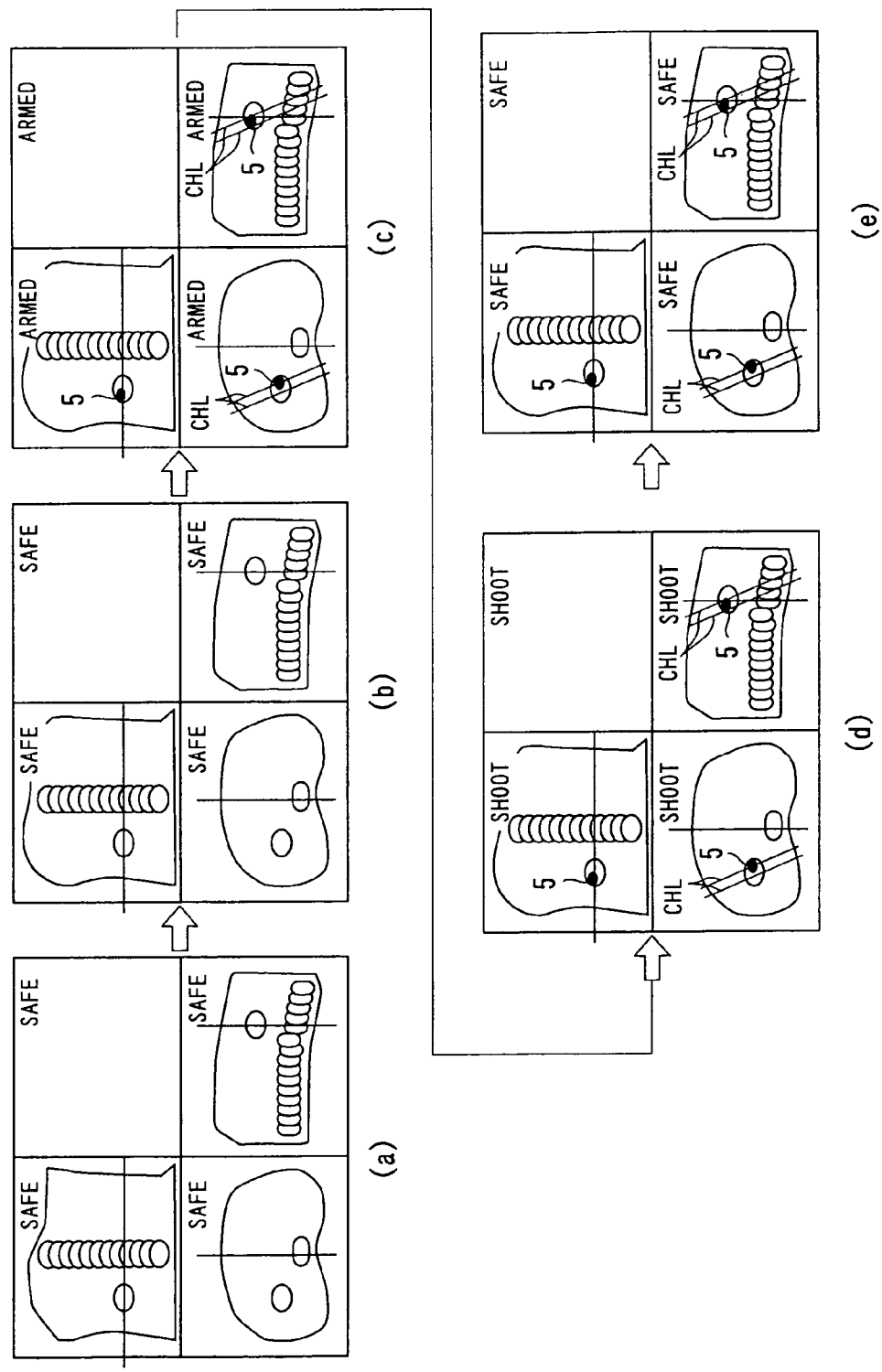
FIG. 9 is a view showing the operation procedure of radiotherapy in the same embodiment by changes on the monitor screen.

As shown in (a) of FIG. 9, an image of the irradiation field 5 and its nearby region is acquired by using only the X-ray CT apparatus 30. A doctor checks each sectional view of the irradiation field 5 on the system screen, and defines a contour for image tracking. Mapping of the irradiation field 5 is complete before the start of therapy, so the contour of the irradiation field 5 is defined by a plurality of slices on the basis of this mapping.

As shown in (b) of FIG. 9, the contour of an image of the actual irradiation field 5 is extracted by the image tracking system of the radiotherapy apparatus. Image tracking is started by pattern matching between this extracted contour and the defined contour. The doctor visually checks the status of this image tracking.

As shown in (c) of FIG. 9, after the image tracking stabilizes, the doctor operates a master arm SW to set the system in an armed state. The system displays the target by cross hair lines on the image, and also displays the irradiation volume in red on the same image. Since the image tracking continues, the target and irradiation volume automatically follow the movement of the irradiation field.

As shown in (d) of FIG. 9, irradiation of the therapeutic radiation 3a is started by a trigger operation by the doctor. Since a scheduled irradiation time is determined in the stage of the therapy plan, countdown is started on the screen, and the therapeutic radiation is automatically stopped when the count is zero (time t4). A dose distribution is continuously displayed on the screen, so the doctor keeps pulling the trigger to continue the irradiation while checking this displayed dose distribution. The system alternatively continues image sampling and irradiation of the therapeutic radiation 3a at high speed, thereby continuing image tracking and therapeutic beam irradiation in real time. Even before the countdown becomes zero, if the doctor releases the trigger the therapeutic radiation 3a immediately stops at that timing, to maintain safety.

As shown in (e) of FIG. 9, the doctor puts the master arm SW in the safe position to set the system in the safe state, and moves the irradiation head 10 to the next irradiation position. At the end of the irradiation time of each portal and the end of a series of irradiations, the doctor checks the total dose which is the total of the accumulated exposure doses. The accumulated dose and the accumulate dose distribution in one course are displayed on the screen and stored in a therapy file formed for each patient.

In this embodiment as described above, the conditions such as the irradiation position and irradiation time can be controlled with high accuracy while the irradiation field is monitored by the X-ray CT apparatus 30. Accordingly, the embodiment is not only applicable to a therapy of the head in which no organ moves, but also a small focus of an organ which moves, such as a heart or lung, can be accurately irradiated. Therefore, this technology is expected to have wide applications in the field of radiotherapy.

Also, this embodiment can use a high-strength, high-rigidity irradiation head supporting structure, as opposed to a cantilevered robot arm, which has rigidity having many problems. This makes it possible to mechanically ensure high absolute accuracy. This obviates the need for teaching required to assure necessary positioning accuracy by using a robot arm, and allows an efficient therapy.

Conventionally, applying a general-purpose, industrial robot arm having an excess degree of freedom which far exceeds a necessary degree of freedom to non-isocentric radiotherapy has a problem in patient safety. That is, if an accident such as an operation error of the robot arm occurs, the robot arm or the irradiation head at the front end of the robot arm may contact a patient to cause traumatic damage to the patient. By contrast, in the radiotherapy apparatus of this embodiment, the movable ranges of the irradiation head support mechanism and the irradiation head itself are mechanically restricted. This assures absolute safety for the patient.

In the prior art, a doctor cannot monitor the irradiation field in real time during radiotherapy, so irradiation based upon presumption is unavoidable. However, in the radiotherapy apparatus of this embodiment, a doctor can monitor the irradiation field in real time during radiotherapy by using the image acquiring apparatus such as an X-ray fluoroscopic apparatus, X-ray CT apparatus, PET, or DSA. This allows highly reliable and safe radiotherapy. Also, on the basis of the image of the irradiation field obtained in real time as described above, it is possible to track the image, and follow and irradiate the moving irradiation field.

Furthermore, the radiotherapy apparatus of this embodiment achieves a man-machine interface with a doctor. Accordingly, radiotherapy superior in safety and reliability can be performed.

(Second Embodiment)

Figure 10:
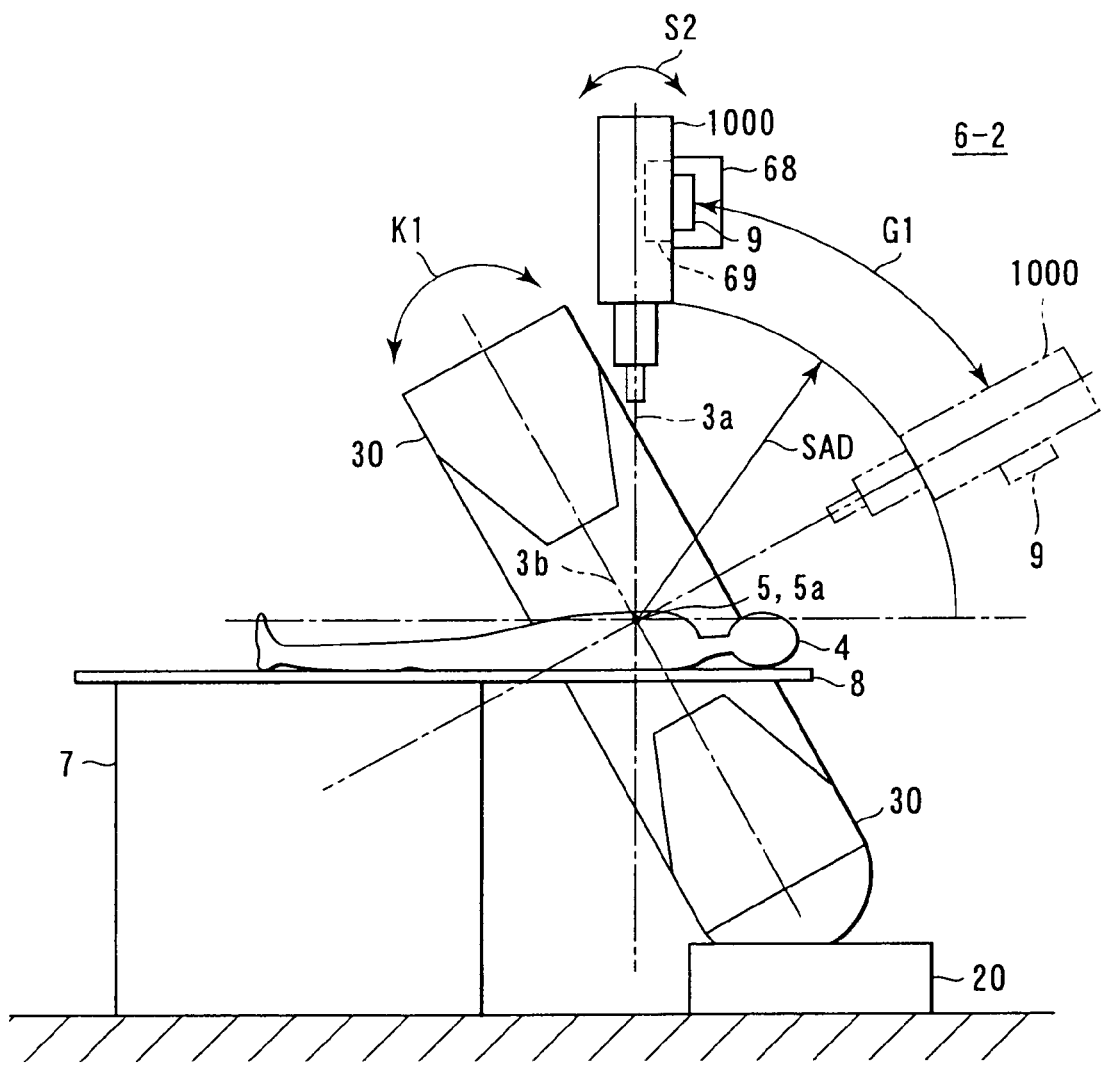
FIG. 10 is a view showing a radiotherapy apparatus according to the second embodiment of the present invention in a direction perpendicular to the bed axis.
Figure 11:
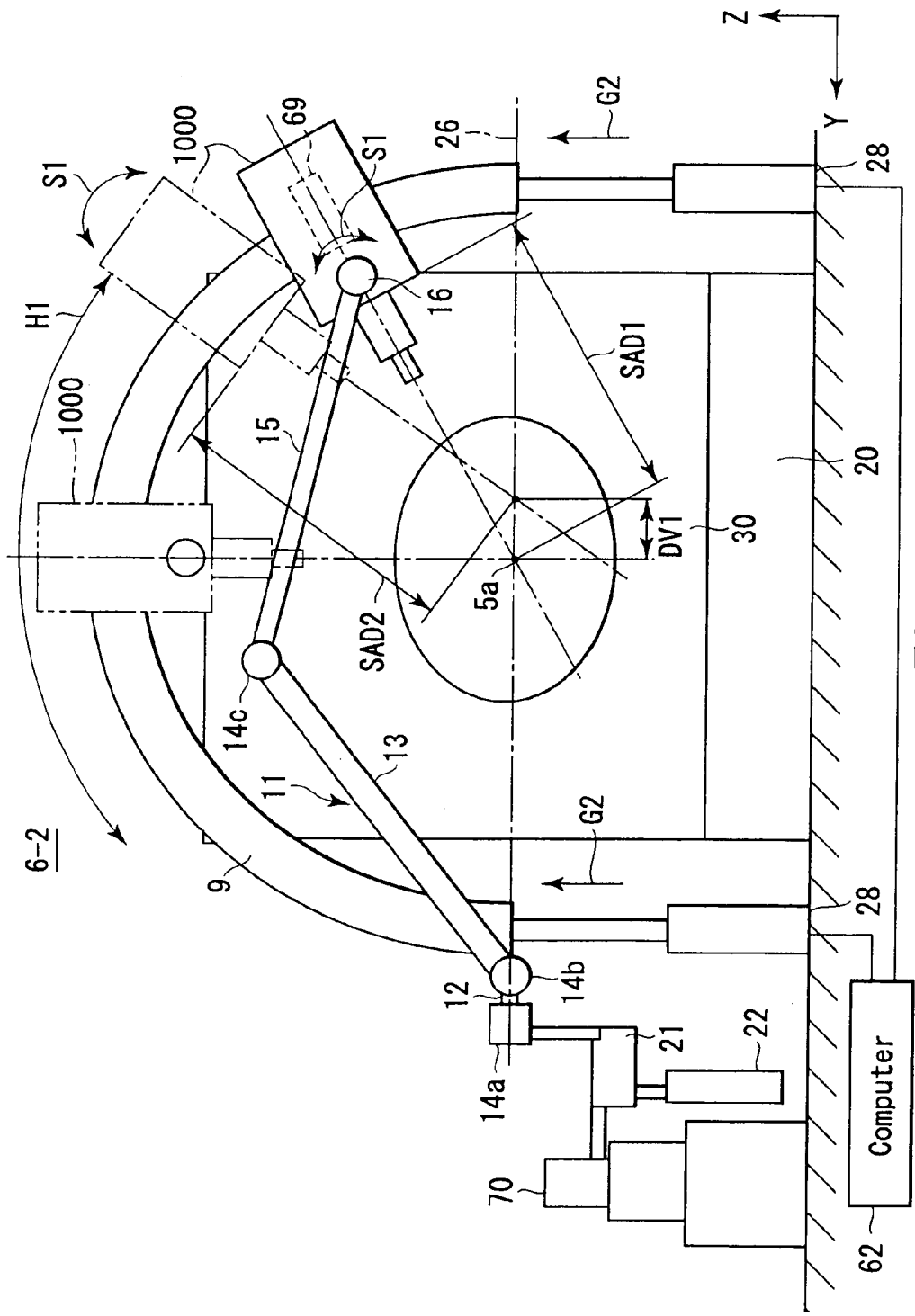
FIG. 11 is a view showing the radiotherapy apparatus of the same embodiment in the bed axis direction.
Figure 12:
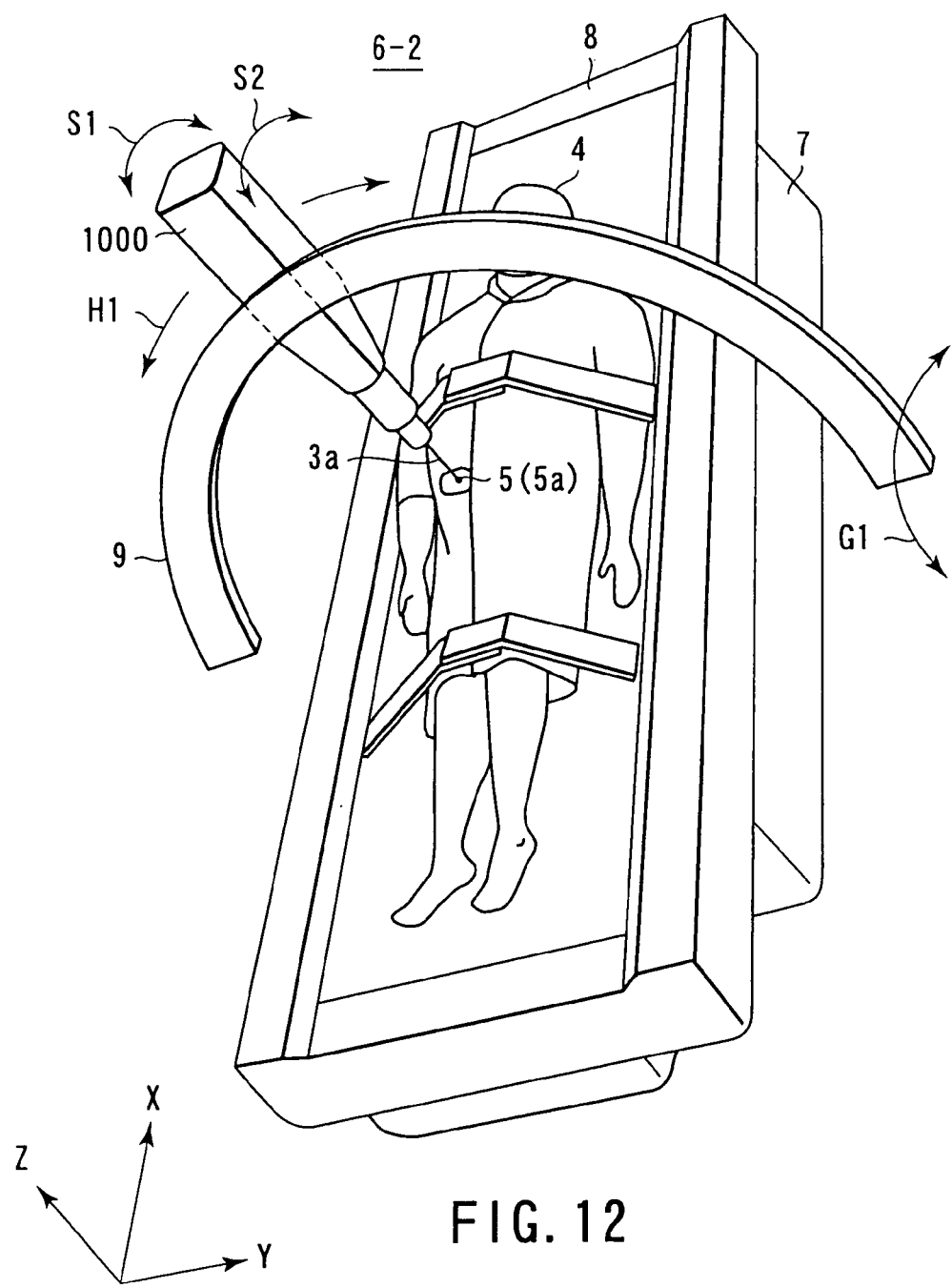
FIG. 12 is a perspective view for explaining radiotherapy performed by the radiotherapy apparatus of the same embodiment.
Figures 13A, 13B, 13C:
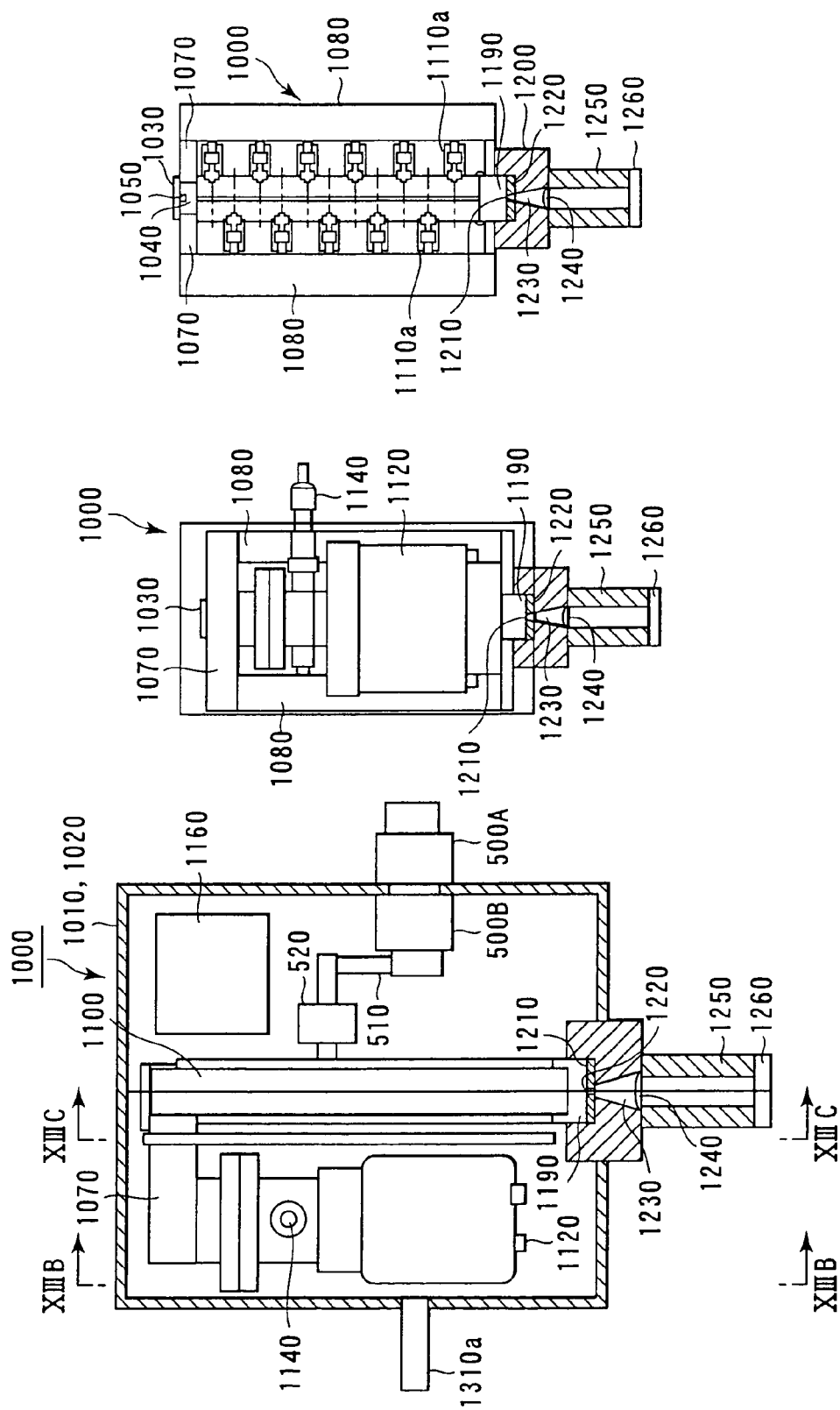
Figure 21:
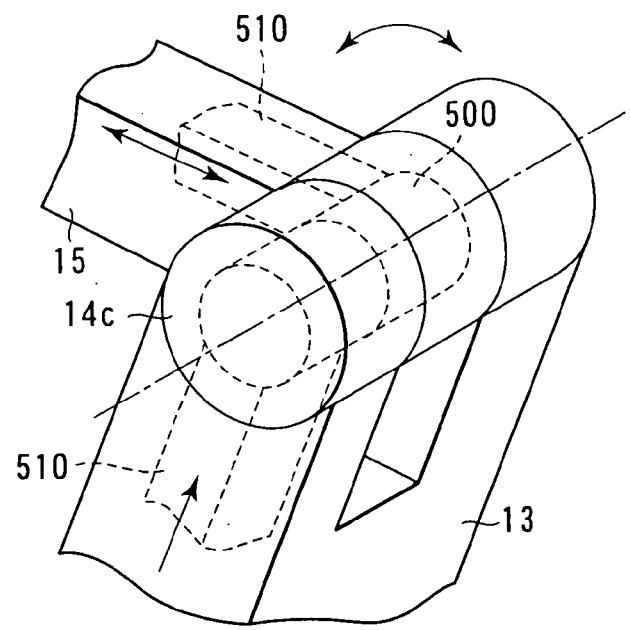
FIG. 21 is a perspective view showing a waveguide system and rotary RF coupler of the radiotherapy apparatus of the same embodiment.
Figure 22:
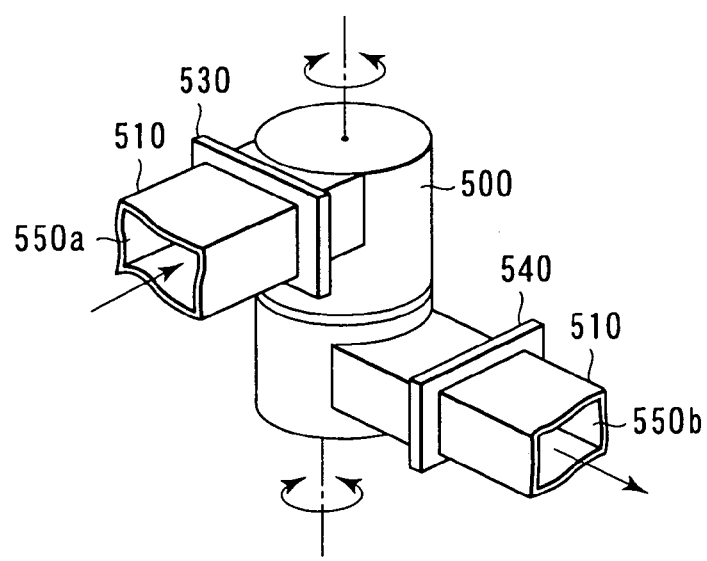
FIG. 22 is a perspective view showing the rotary RF coupler and waveguides of the radiotherapy apparatus of the same embodiment.

A radiotherapy apparatus 6-2 of the second embodiment of the present invention will be described below with reference to FIGS. 10 to 25 in which the same reference numerals as in FIGS. 1 to 9 denote the same parts. FIGS. 10 to 12 correspond to FIGS. 1 to 3, FIG. 18 corresponds to FIG. 8, FIGS. 21 and 22 correspond to FIGS. 5 and 6, and FIG. 25 corresponds to FIG. 9. Therefore, a repetitive explanation of the same portions will be omitted.

As shown in FIGS. 10 to 12 and 20A to 20D, an irradiation head 1000 of this embodiment is supported by a guide rail 9 by a circumferential moving mechanism 68 and first and second head rotating mechanisms 1310 and 1320. These circumferential moving mechanism 68 and first and second head rotating mechanisms 1310 and 1320 position the irradiation head 1000 in an arbitrary irradiation position within the range of a quarter sphere (half sphere) of the rear portion of the upper half of a sphere around an isocenter 5a.

The circumferential moving mechanism 68 circumferentially moves (H1) the irradiation head 1000 along the guide rail 9 by, e.g., a rack and pinion system or belt system.

As shown in FIGS. 20A to 20D, the first head rotating mechanism 1310 includes a servo motor, and rotates the irradiation head 1000 on the guide rail 9 around a first axis S1 of a rotary RF coupler 16. This rotary RF coupler 16 is placed on an axis substantially passing through the center of inertia of the irradiation head 1000, so that the inertial force decreases when the irradiation head 1000 rotates.

As shown in FIGS. 20A to 20D, the second head rotating mechanism 1320 includes a servo motor, and rotates the irradiation head 1000 on the guide rail 9 around a second axis S2 of rotary RF couplers 500A and 500B. These rotary RF couplers 500A and 500B placed on an axis substantially passing through the center of inertia of the irradiation head 1000, so that the inertial force decreases when the irradiation head 1000 rotates. The irradiation head 1000 of this embodiment has a total length of 500 to 600 mm, width 500 mm×depth 300 mm, and a weight of 60 to 80 kg.

This irradiation head 1000 is rotatably coupled with the rotary RF coupler 16 of a waveguide system 11. The irradiation head 1000 is connected to a microwave oscillator 70 by waveguides 510 and rotary RF couplers 500 on a gimbal mechanism shown in FIG. 20A.

Biaxial driving (G1 and H1) described above permits isocentric motion of the irradiation head 1000 on the half sphere around the isocenter 5a. In addition, biaxial driving (S1 and S2) described above permits pseudo non-isocentric motion of the irradiation head 1000 on the half sphere.

This pseudo non-isocentric motion is the rotation of the irradiation head 1000 around the center of inertia, and hence is much faster than the isocentric motion. This pseudo-isocentric, high-response, rapid tracking motion allows the head to follow and aim at even a rapid motion such as heartbeat with high response and high precision.

Figure 15:
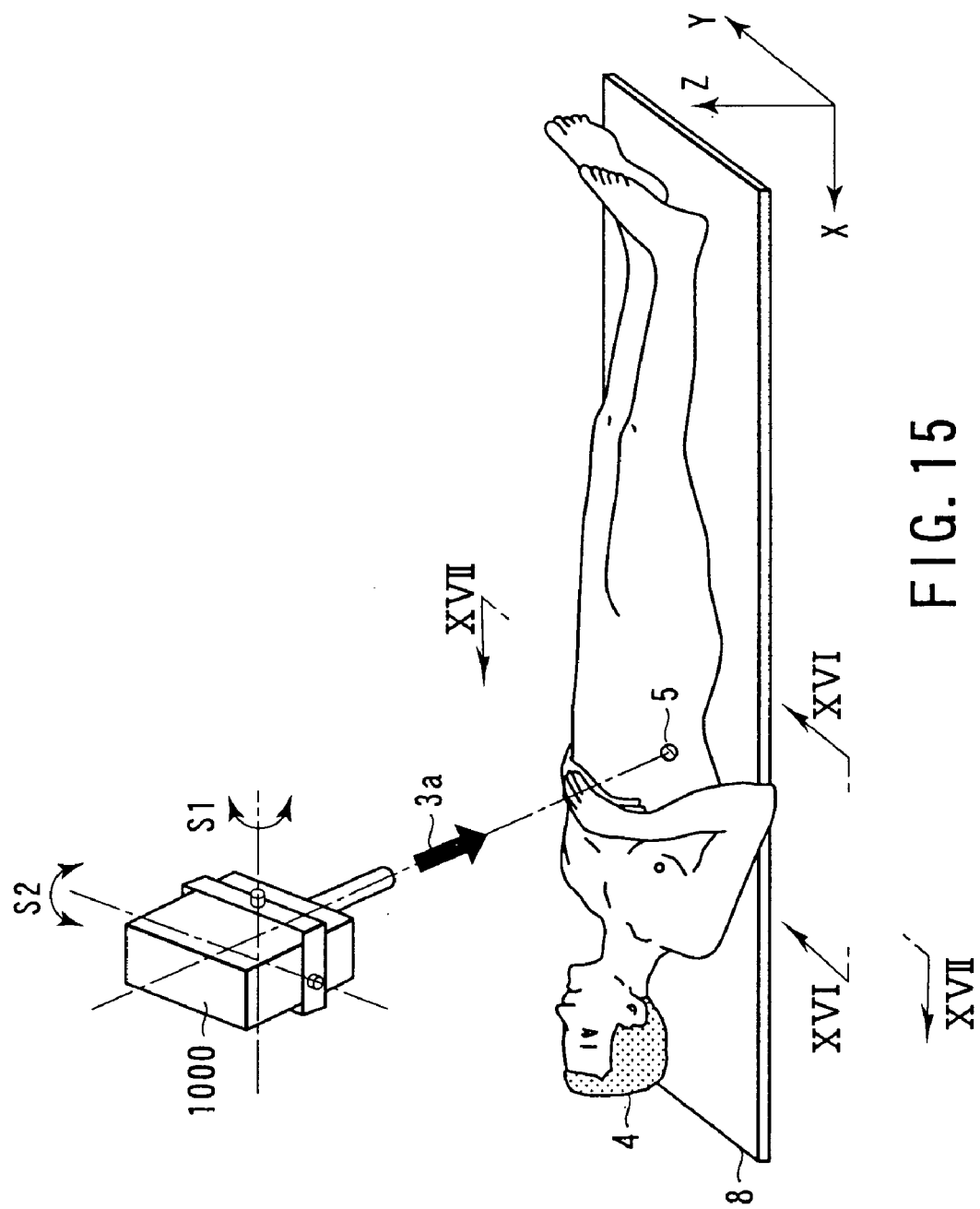
FIG. 15 is a perspective view showing the irradiation head and a patient when pseudo non-isocentric radiotherapy is performed by the radiotherapy apparatus of the same embodiment.
Figure 16:
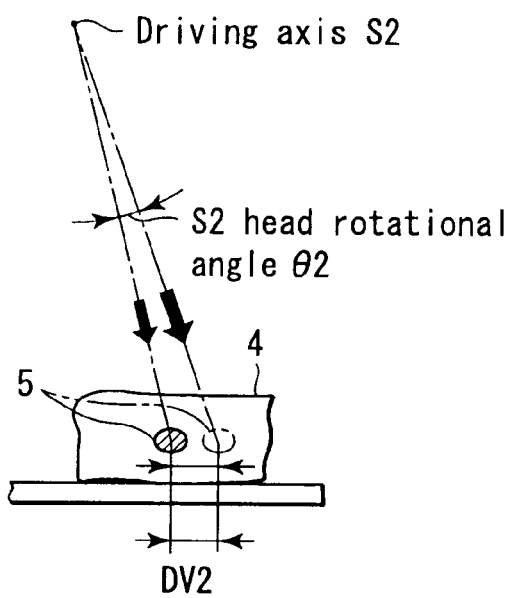
FIG. 16 is a partial sectional view taken along a line XVI—XVI in FIG. 15, for explaining an example of a head rotating operation of the irradiation head when pseudo non-isocentric radiotherapy is performed by the radiotherapy apparatus of the same embodiment.
Figure 17:
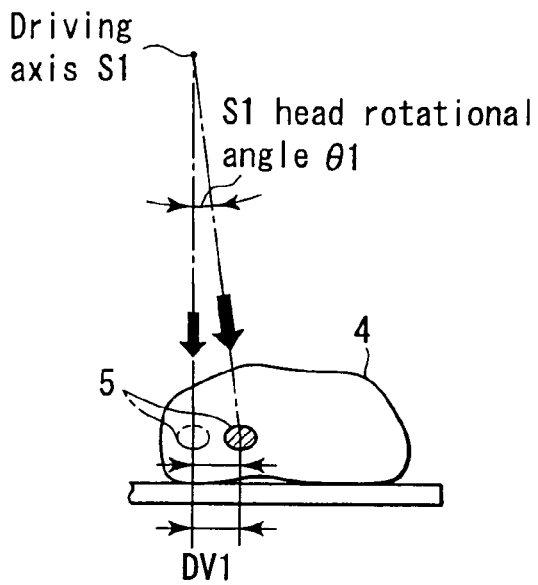
FIG. 17 is a partial sectional view taken along a line XVII—XVII in FIG. 15, for explaining another example of the head rotating operation of the irradiation head when pseudo non-isocentric radiotherapy is performed by the radiotherapy apparatus of the same embodiment.

In this embodiment, to follow the movement of the irradiation field and irradiate the field, as shown in FIGS. 15, 16, and 17, a microdisplacement angle θ1 around the head rotation driving axis S1 and a microdisplacement angle θ2 around the head rotation driving axis S2 are calculated by shift amounts DV1 and DV2 obtained from image data and predetermined expressions. In accordance with the calculation result, driving of the head rotating mechanisms 1310 and 1320 is controlled to rotate the irradiation head 1000 through the microdisplacement angles θ1 and θ2 at high speed. Accordingly, the irradiation head 1000 can follow and aim, at high speed and high response, at a diseased part 5 below the neck, e.g., a tumor having a motion such as breathing, heartbeat, peristalsis, or the urine amount in a bladder. This realizes high-accuracy irradiation. In the radiotherapy apparatus of this embodiment, the irradiation head 1000 can be rotated at high speed within 0.1 sec including the acquired image processing time. This allows the irradiation head 1000 to rapidly follow the movement of the irradiation field (diseased part).

Figures 23A, 23B:
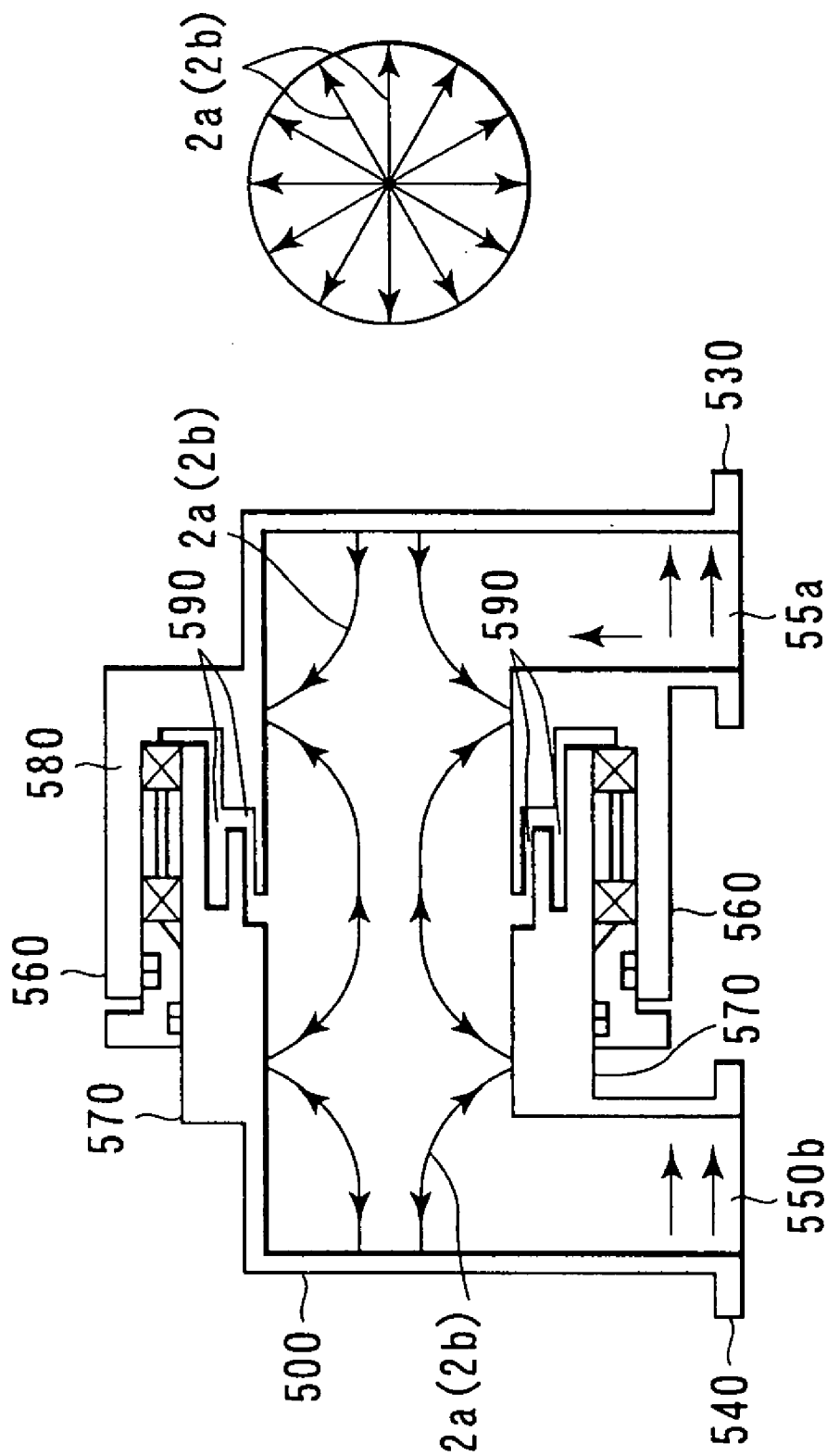
FIGS. 23A and 23B are views for explaining the rotary RF coupler of the radiotherapy apparatus of the same embodiment.

As shown in FIG. 23A, waveguides 550a and 550b of the waveguide 510 communicate with a rotating space surrounded by rotary members 560 and 570 of the rotary RF coupler 500. In this rotating space, microwaves are guided in a waveguide mode as shown in FIG. 23B.

When tomographic image data of the irradiation field 5 is input from an X-ray CT apparatus 30 as an image acquiring apparatus, a system controller 80 controls driving of the circumferential moving mechanism 68, a tilting mechanism, and a bed 7 on the basis of this data, thereby aiming the irradiation head 1000 at the irradiation field 5 in the isocenter 5a.

If this irradiation field 5 moves, the system controller 80 performs calculations for image tracking on the basis of input data from the X-ray CT apparatus 30. On the basis of the calculation results, the system controller 80 controls the operations of the first and second head rotating mechanisms 1310 and 1320, thereby rotating the irradiation head 1000. While the irradiation head 1000 is rotated, an interlock operates to inhibit irradiation. This minimizes the exposure dose in a nearby portion.

Details of the irradiation head 1000 of this embodiment will be explained below.

As shown in FIGS. 13A to 13C and 19, a main body of this irradiation head 1000 is covered with a cover 1010, and an emitting portion 1200 for emitting radiation is attached to the front end of this head main body. The cover 1010 for covering the head main body contains an electric circuit/cooling water circuit 1160, an accelerator 1100, an RF window 520, the waveguide 510, the part 500B of the rotary RF coupler, an exhaust pipe 1070, an ion pump 1120, a target exhaust chamber 1190, a target 1210, and a cooling plate 1220. Also, a cable (not shown) connected to an external power supply is introduced into the cover 1010 from an insulator 1030 at the rear end of the accelerator 1100, and connected to a cathode 1050 of an electron gun 1040. An anode 1060 faces this cathode 1050. A portion between the cathode 1050 and anode 1060 is exhausted by the exhaust pipe 1070 which communicates with the ion pump 1120. A power supply of the electron gun 1040 is controlled by the system controller 80. The electron gun 1040 continues from the accelerator 1100 to the emitting portion 1200. The length from the insulator 1030 to the front end of the accelerator 1100 is about 360 mm.

Figure 14:
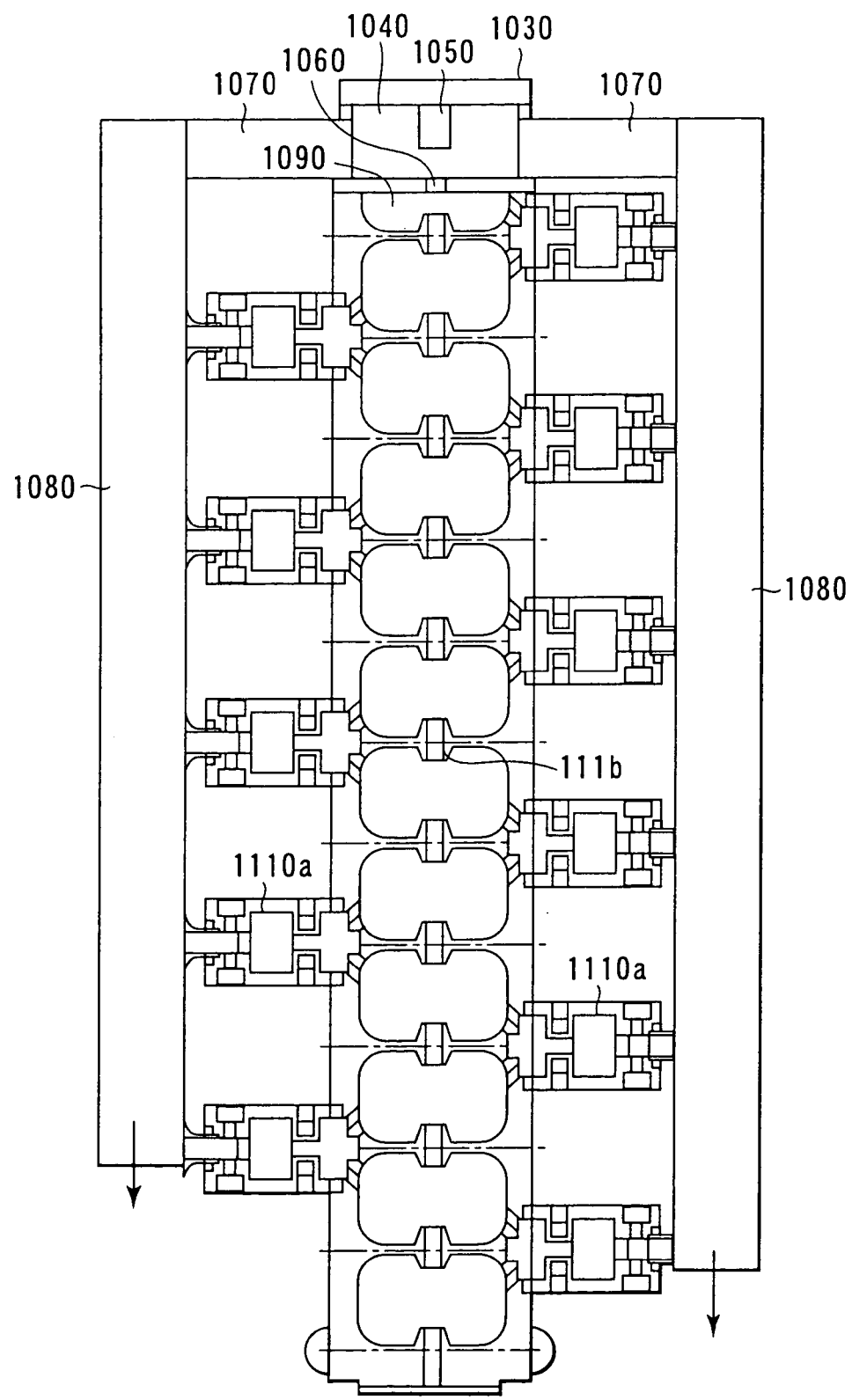
FIG. 14 is a view showing a subminature C-Band accelerator of the irradiation head of the radiotherapy apparatus of the same embodiment.

As shown in FIG. 14, a central hole in the anode 1060 of the electron gun 1040 communicates with a buncher cavity 1090 of the accelerator 1100. The accelerator 1100 accelerates an electron beam emitted from the electron gun 1040, and collides the high-energy electron beam against the X-ray target 1210. In this accelerator 1100, an acceleration cavity 1110b having a central hole for passing the electron beam is formed. This acceleration cavity 1110b communicates with a pair of left and right side exhaust pipes 1080 via side couple cavities 1110a. The pair of left and right side exhaust pipes 1080 are connected to the ion pump 1120. Accordingly, the pair of left and right side exhaust pipes 1080 are evacuated by the ion pump 1120. That is, the accelerator 1100 is evacuated by the ion pump 1120 via the side couple cavities 1110*a* and side exhaust pipes 1080.

The waveguide 510 communicates with the accelerator 1100. This waveguide 510 communicates with the microwave oscillator 70 via the ceramic RF window 520 and rotary RF couplers 500A and 500B. The RF window 520 prevents leakage of $SF_6$ gas sealed in the waveguide 510, and functions as an entrance for introducing microwaves into the accelerator 1100. The microwave oscillator 70 is a klystron type oscillator superior in output stability. A power supply circuit of this microwave oscillator 70 is connected to the system controller 80.

The emitting portion 1200 is formed at the end portion of the head main body covered with the cover 1010, and includes the X-ray target 1210, the target cooling plate 1220, a primary collimator 1230, and a flattening filter 1240. Components from the electron gun 1040 to the flattening filter 1240 via the accelerator 1100 are arranged in series along the optical axis of the electron beam. The accelerated electron beam is incident on the target 1210 of the emitting portion 1200 through the target exhaust chamber 1190.

The X-ray target 1210 receives high-energy accelerated electrons and outputs bremsstrahlung X-rays. Therefore, this X-ray target 1210 is readily damaged by heat. As a countermeasure against this heat, the cooling plate 1220 cools the X-ray target 1210. As this target 1210, a refractory metal such as tungsten, molybdenum, or tantalum, or an alloy of any of these metals is used.

The primary collimator 1230 is made of a material, such as tungsten, which is superior in shielding properties against radiation and generates few thermal neutrons. This primary collimator 1230 guides X-rays from the target 1210 to the flattening filter 1240.

The flattening filter 1240 forms therapeutic radiation 3*a* having a uniform dose distribution by averaging the intensities of X-rays emitted from the target 1210.

Furthermore, a secondary collimator 1250 and dose measurement ionization chamber 1260 are attached to the front end of the emitting portion 1200. The secondary collimator 1250 is made of a highly shielding material, such as tungsten, through which the therapeutic radiation 3*a* cannot pass, and supplies the therapeutic radiation 3*a* to the dose measurement ionization chamber 1260 through a hollow portion. This secondary collimator 1250 is detachably screwed into the end face of the primary collimator 1230.

The dose measurement ionization chamber 1260 is an ionization chamber which is attached to the end portion of the secondary collimator 1250, and in which a gas having a predetermined component is sealed. A detection circuit (not shown) for detecting discharged electric charge is connected to this dose measurement ionization chamber 1260. This detection circuit is connected to the input of the system controller 80. On the basis of an input signal from the dose measurement ionization chamber 1260, the system controller 80 calculates the dose of the therapeutic radiation emitted from the irradiation head 1000, and saves the calculated dose in a memory as dose data of a therapy which a patient 4 undergoes.

Figure 18:
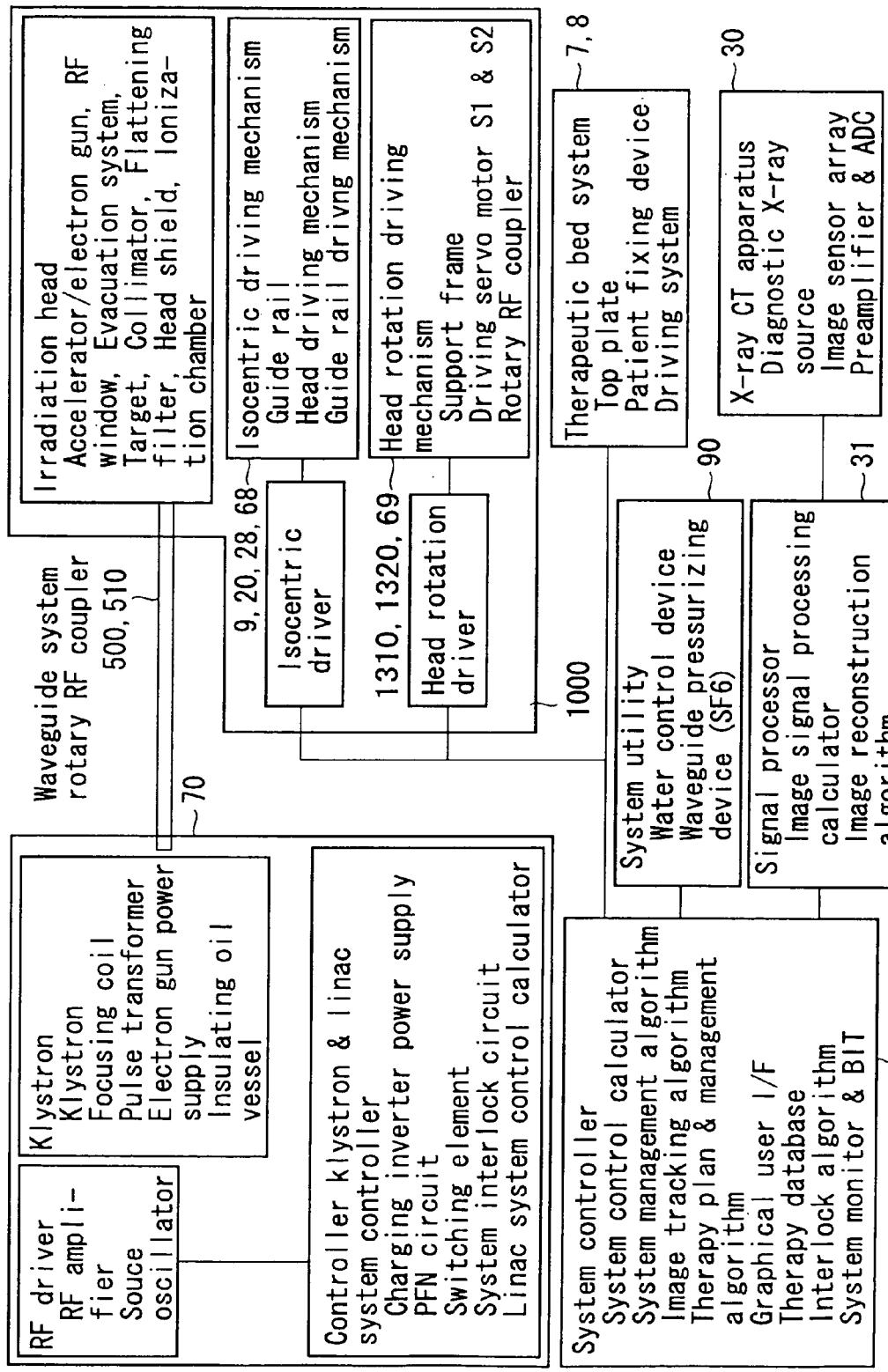
FIG. 18 is a block diagram of the radiotherapy apparatus according to the same embodiment of the present invention.

A control system of the radiotherapy apparatus of this embodiment will be described below with reference to FIG. 18.

The control system of the apparatus of this embodiment includes a bed 8, the irradiation head 1000, the X-ray CT apparatus 30, a signal processor 31, the microwave oscillator 70, the system controller 80, and a system utility 90. The system controller 80 controls the whole system.

This system controller 80 includes a system control calculator, system management algorithm, image tracking algorithm, therapy plan algorithm, therapy management algorithm, graphical user interface, therapy database, interlock algorithm, and system monitor.

The X-ray CT apparatus 30 is connected to the system controller 80 via the signal processor 31. Accordingly, images are acquired in real time during a therapy, so a doctor can perform the therapy while monitoring the acquired images on the display.

The microwave oscillator 70 comprises a klystron modulator and linac system controller, a klystron, and an RF driver. The klystron which supplies microwaves to the accelerator 1100 is connected to the irradiation head 1000 via the waveguide system 11.

The isocentric driving mechanism and head rotating mechanisms of the irradiation head 1000 are connected to the system controller 80. The circumferential moving mechanism 68 is controlled during isocentric irradiation, and the biaxial head rotating mechanisms 1310 and 1320 are controlled during pseudo non-isocentric irradiation.

The head rotating mechanisms of this embodiment will be described in detail below with reference to FIGS. 15 to 17, 19, and 20A to 20D.

Figure 19:
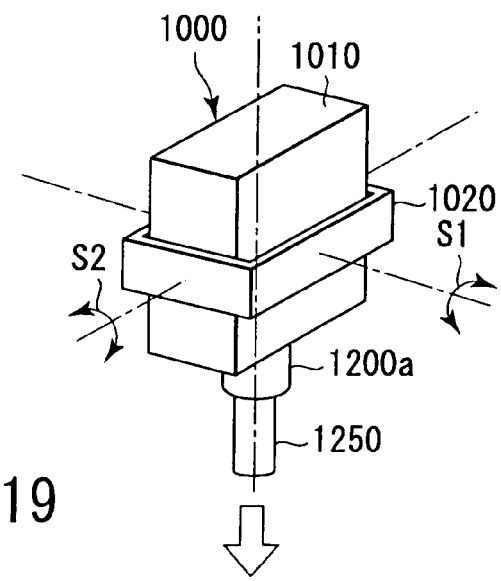
FIG. 19 is a perspective view showing the irradiation head of the radiotherapy apparatus according to the same embodiment of the present invention.

As shown in FIG. 19, the irradiation head 1000 of this embodiment is supported by a gimbal structure support frame 1020 of the head cover 1010. This support frame 1020 is positioned at coordinates where the axes S1 and S2 including the center of inertia of the irradiation head 1000 pass by.

Figure 20A:
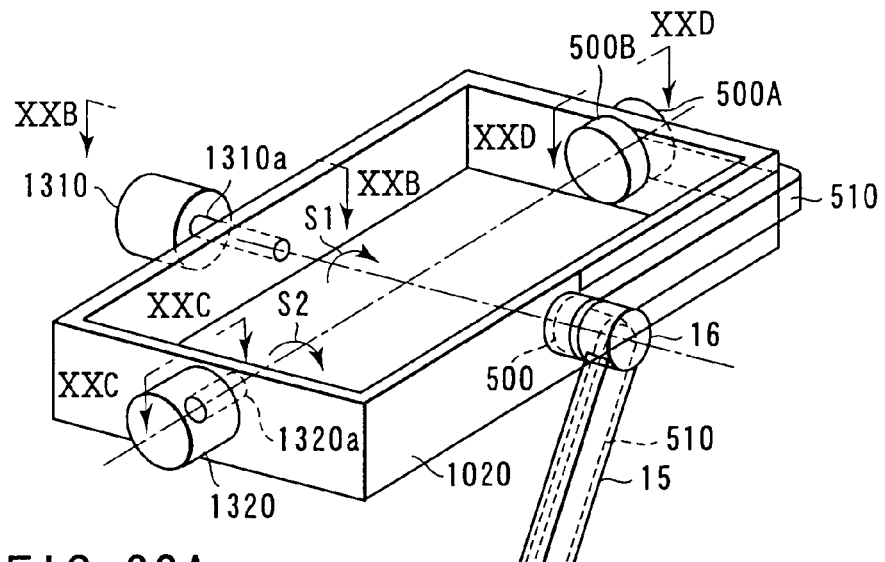

As shown in FIG. 20A, the rotary RF coupler 16 of the waveguide system 11, the pair of rotary RF couplers 500A and 500B, the S1 head rotating mechanism 1310 which is a servo motor, and the S2 head rotating mechanism 1320 which is also a servo motor are attached to the four sides of the support frame 1020.

Figure 20B:
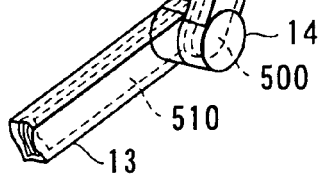

As shown in FIG. 20B, the rotary RF coupler 16 of the waveguide system 11 is attached to the center of one long side of the support frame 1020. A driving shaft 1310*a* of the S1 head rotating mechanism 1310 is attached to the center of the opposite long side of the frame 1020 so as to face the rotary RF coupler 16. When this driving shaft 1310*a* is rotated, as shown in FIG. 17, the irradiation head 1000 rotates around the driving axis S1.

Figure 20C:
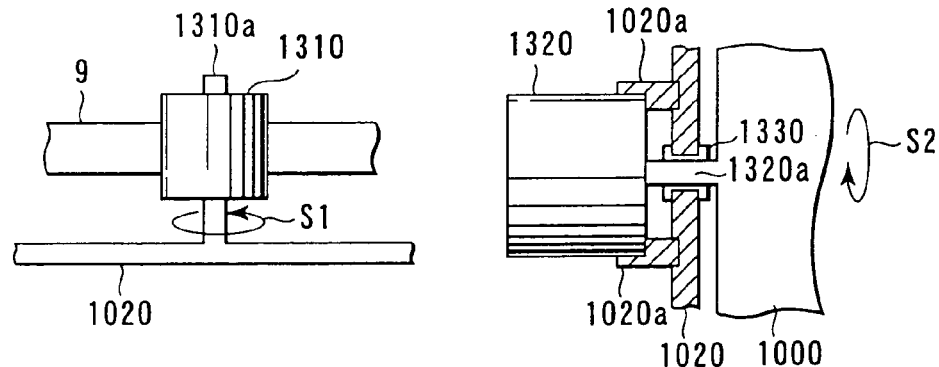
Figure 20D:
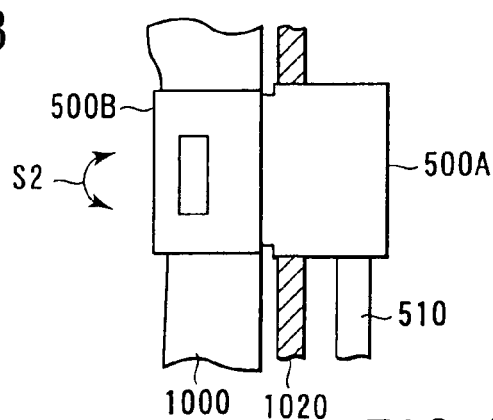

As shown in FIG. 20D, the pair of rotary RF couplers 500A and 500B are attached to the center of one short side of the support frame 1020.

As shown in FIG. 20C, a driving shaft 1320*a* of the S2 head rotating mechanism 1320 is attached to the center of the opposite short side of the frame 1020 so as to face the pair of rotary RF couplers 500A and 500B. That is, the main body of the S2 head rotating mechanism 1320 is fixed to a bracket 1020*a* of the support frame 1020, and the driving shaft 1320*a* is rotatably supported by the support frame 1020 via a bearing 1330. When this driving shaft 1320*a* is rotated, as shown in FIG. 16, the irradiation head 1000 rotates around the driving axis S2.

As shown in FIG. 20A, the waveguides 510 are formed in link arms 13 and 15 of the waveguide system 11. The rotary RF couplers 500 are formed in joints 14 and 16. Microwaves are introduced into the accelerator 1100 in the irradiation head through the pair of rotary RF couplers 500A and 500B.

The operation of the radiotherapy apparatus 6-2 of this embodiment, particularly, a method of preventing the influence which direct rays, leakage rays, and scattered rays of therapeutic radiation have on a detector, thereby realizing real-time, time-divisional processing of irradiation of image acquiring X-rays and irradiation of therapeutic radiation, will be explained below with reference to a timing chart shown in FIG. 24.

First, when the main switch of the radiotherapy apparatus 6-2 is turned on, the power supplies of the therapeutic bed system 7, irradiation head 1000, X-ray CT apparatus 30, microwave oscillator 70, system controller 80, and system utility 90 are set in a standby state. The top plate 7 moves to move the patient 4 into a therapy area. More specifically, the diseased part 5 is aligned with the isocenter 5a by moving the X-ray CT apparatus 30 and/or the bed 8. After this isocentric alignment is completed, real-time image acquisition by the X-ray CT apparatus 30 and radiotherapy by the irradiation head 1000 are started.

Figure 24:
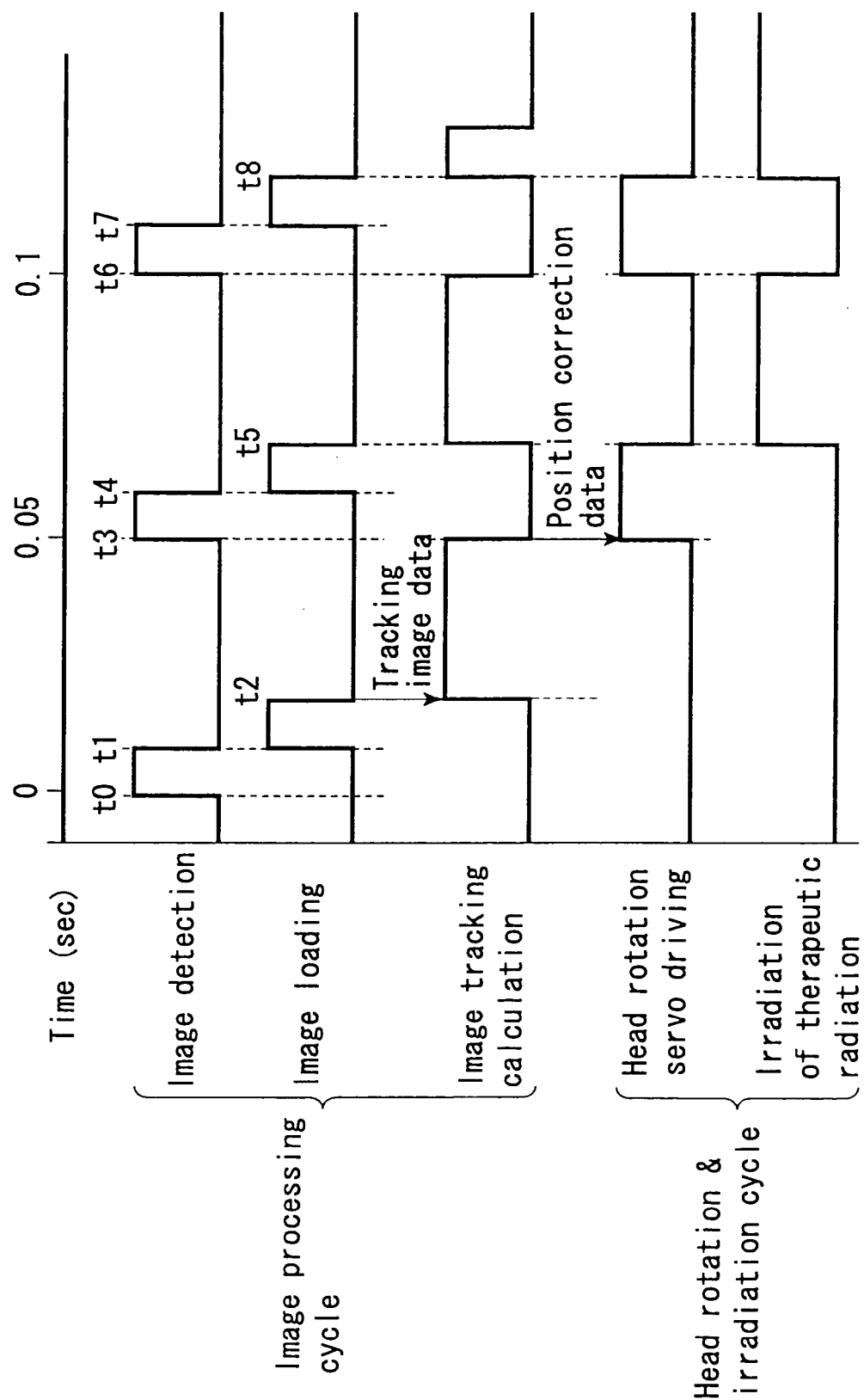
FIG. 24 is a timing chart showing the operation of the same embodiment.

At time t0 in FIG. 24, the X-ray CT apparatus 30 starts irradiating the irradiation field 5 with image acquiring X-rays 3b. The fluoroscopic image is detected as an acquired image at time t0 to time t1 shown in FIG. 24. To minimize the exposure, the irradiation time of the image acquiring X-rays 3b is also limited between time t0 and time t1. Furthermore, to prevent the influence which direct rays, leakage rays, and scattered rays of the therapeutic radiation 3a have on the detector in at least time t0 to time t1 during which the image acquiring X-rays 3b are emitted, the irradiation head 1000 is interlocked so as not to emit the therapeutic radiation 3a.

The detected acquired image is loaded (recorded) at time t1 to time t2. At time t2 to time t3, information such as tracking image data of the loaded acquired image is processed by the signal processor 31 and system controller 80, and the processed image is displayed on the display. Also, the information processed by this image tracking calculation is supplied as position correction data to the head rotating mechanisms 1310 and 1320. The same cycle from image acquisition to image processing as in time t0 to time t3 is repeated after time t3.

While the next image detection and image acquisition are performed at time t3 to time t5, the head rotating servos of the head rotating mechanisms 1310 and 1320 are driven through the micro-head-rotating angles θ1 and θ2 on the basis of the result of the image tracking calculation supplied as the position correction data. At time t3 to time t5 during which the head rotating mechanisms 1310 and 1320 are driven, to ensure safety, the irradiation head 1000 is interlocked so as not to emit therapeutic radiation 3a.

At time t5 at which the head rotating mechanisms 1310 and 1320 stop, the irradiation head 1000 is released from interlocking and starts emitting the therapeutic radiation 3a. The irradiation time of the therapeutic radiation 3a is time t5 to time t6 before the head rotating mechanisms 1310 and 1320 are driven next. In synchronism with time t5 to time t6, an image tracking calculation is executed for the tracking image data of the image acquired between time t3 and t5. At time t6, third image detection and second head rotating servo driving are started, and the second image tracking calculation and the first irradiation of the therapeutic radiation 3a are complete.

After the irradiation of the therapeutic radiation 3a is stopped, irradiation of the image acquiring X-rays 3b is started at time t6 to proceed to the next acquired image processing cycle beginning from time t6. At timing t8 after the third image loading from time t0, the irradiation head 1000 is released from interlocking, and the second irradiation of the therapeutic radiation 3a is restarted.

As described above, the image processing cycle and the head rotating and irradiation cycle overlap each other. While a certain image processing cycle is performed, a cycle of head rotational driving and irradiation of the therapeutic radiation 3a is performed on the basis of information of an image processing cycle executed immediately before this image processing cycle.

To follow a rapid motion such as heartbeat, one standard of time t0 to time t6 from the start of image detection to the end of irradiation of the therapeutic radiation 3a via rotation of the irradiation head 1000 is 0.1 sec or less. In the timing chart shown in FIG. 24, therefore, one cycle of image processing and one cycle of head rotation and irradiation are 0.05 sec. Accordingly, the times in the timing chart shown in FIG. 24 are merely examples, so the operation can also be carried out at other time intervals.

Also, if abnormality occurs during image acquisition or image tracking calculations, interlocking is performed to stop irradiation of the therapeutic radiation 3a at that point, thereby improving the safety. The radiotherapy apparatus 6-2 of this embodiment is so designed as to emit the therapeutic radiation 3a after it is confirmed that rotation and positioning of the irradiation head 1000 are normally executed.

In the radiotherapy apparatus 6-2 of this embodiment as described above, the image detection cycle, the image loading cycle, the image tracking calculation cycle, the head rotation control cycle based on the image tracking calculation cycle, and the therapeutic radiation 3a emission cycle are repeated, and a therapy is performed by following and irradiating the irradiation field 5 from the position of the half sphere over the bed.

Figure 25:
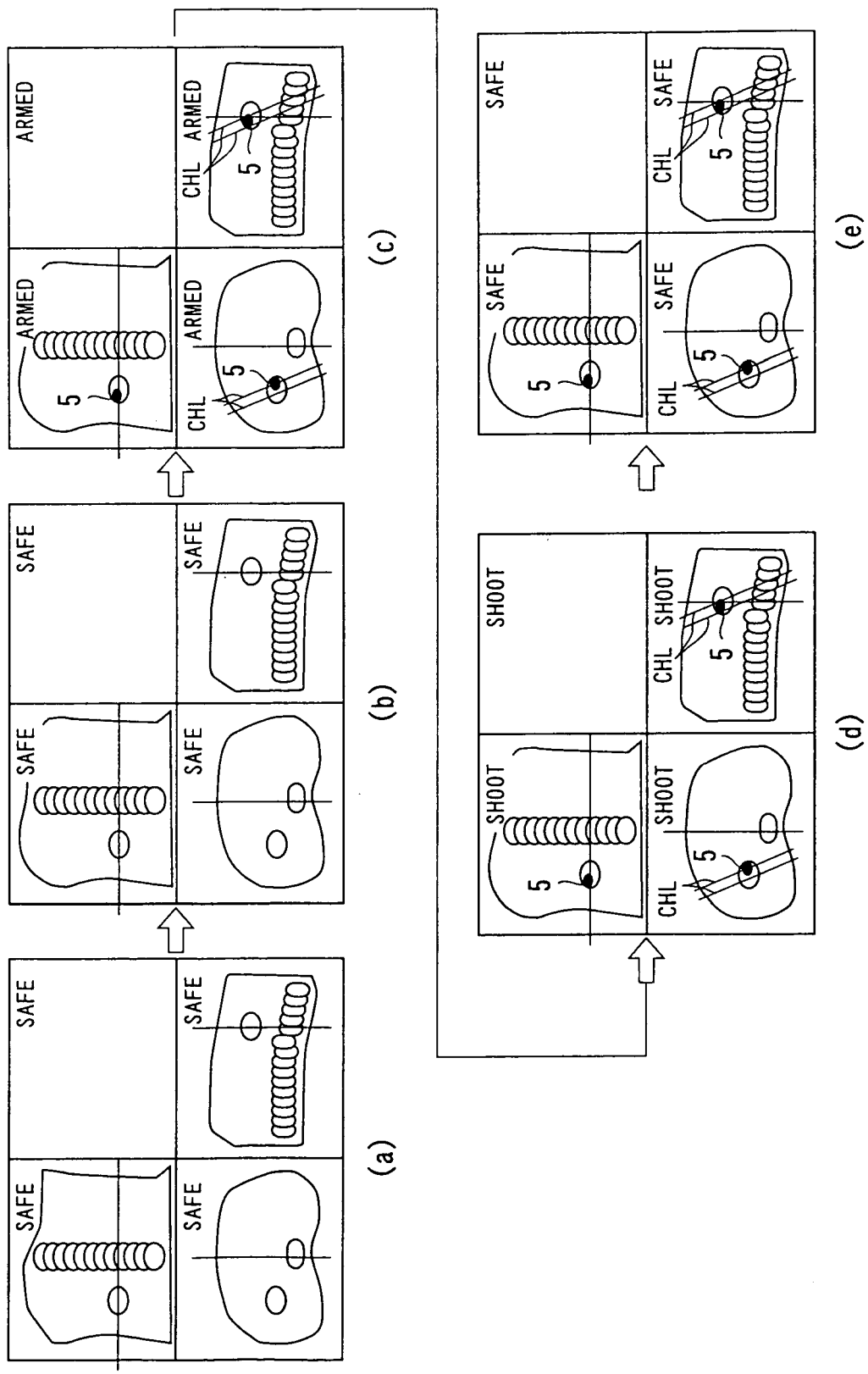
FIG. 25 is a view showing the operation procedure of a radiotherapy in the same embodiment by changes on the monitor screen.

A therapeutic method of the radiotherapy apparatus 6-2 of this embodiment described above is shown in (a) to (e) of FIG. 25. Since FIG. 25 is the same as FIG. 9, a detailed explanation thereof will be omitted.

In the radiotherapy apparatus 6-2 of this embodiment described above, it is possible to rapidly rotate the irradiation head 1000 within 0.1 sec including the image processing time, and allow the irradiation head 1000 to follow the movement of the irradiation field (diseased part). Accordingly, high-accuracy irradiation can be realized.

As described above, the radiotherapy apparatus 6-2 of this embodiment can perform non-isocentric irradiation at high response and high accuracy in accordance with the movement of a diseased part. Therefore, an object to be cured can be a portion below the neck, where an object of irradiation such as a tumor moves under the influence of the motion and state of an organ, e.g., breathing, heartbeat, peristalsis, or the urine amount in a bladder.

(Third Embodiment)

Figure 26:
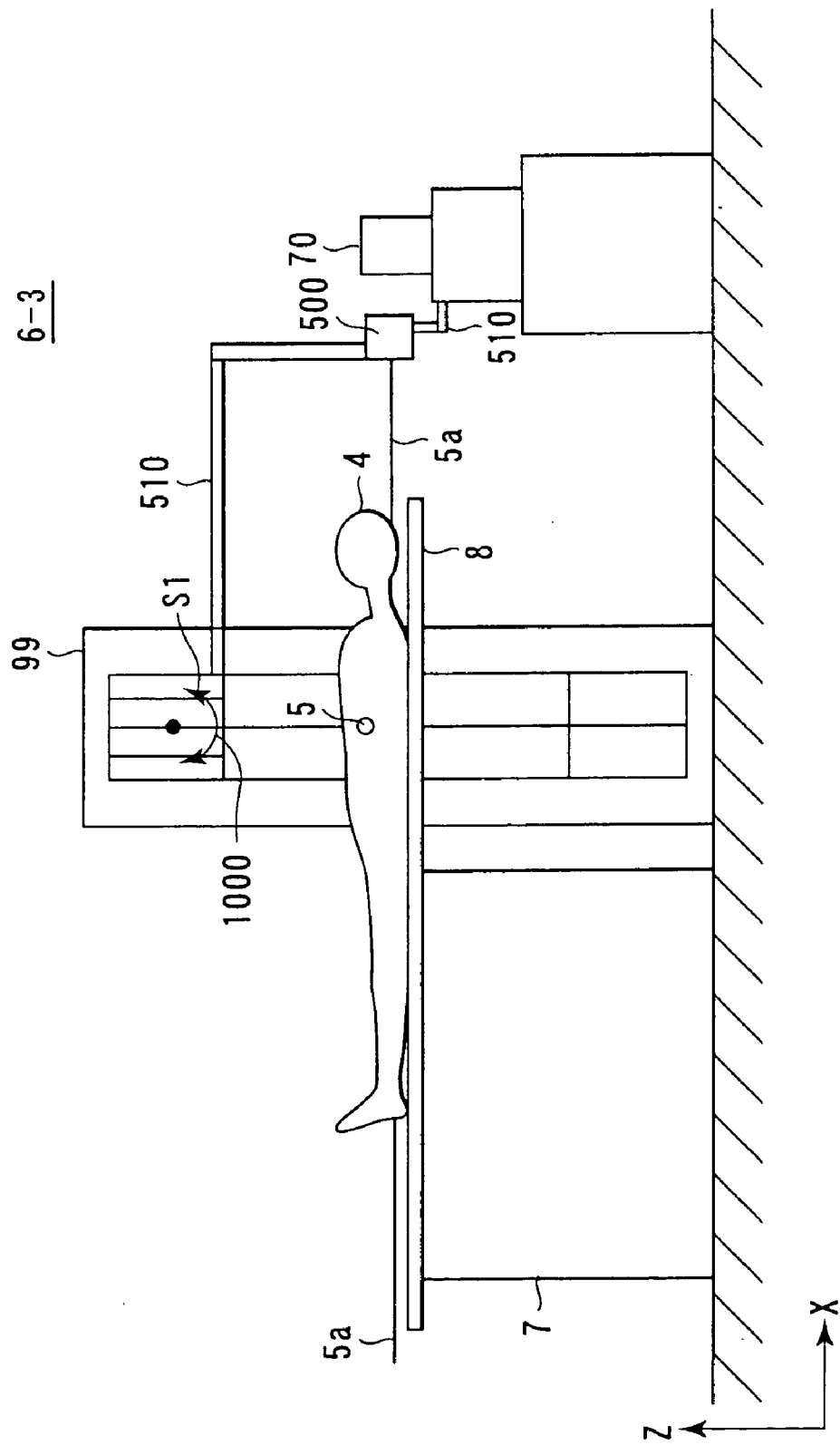
FIG. 26 is a view showing a radiotherapy apparatus according to the third embodiment of the present invention in the direction of the bed axis.
Figure 27:
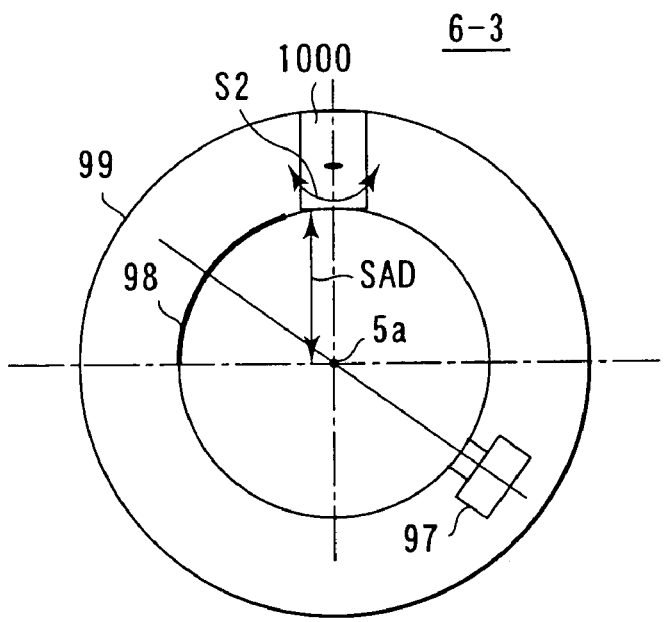
FIG. 27 is a view showing the radiotherapy apparatus of the same embodiment in the bed axis direction.

A radiotherapy apparatus according to the third embodiment of the present invention will be described below with reference to FIGS. 26 and 27. In FIGS. 26 and 27, a repetitive explanation of the same portions as in the previous figures will be omitted.

In a radiotherapy apparatus 6-3 of this embodiment, an irradiation head 1000, an image acquiring X-ray source 97 as an X-ray tube of an X-ray CT apparatus, and a sensor array 98 are mounted on a rotary drum 9. The irradiation head 1000 is mounted on a drum of, e.g., a third-generation X-ray CT apparatus. The rotational center of the rotary drum 99 is an isocenter 5a. The irradiation head 1000 is equivalent to an electron linac which generates a radiation of 4 to 10 MeV. As shown in FIGS. 26 and 27, this irradiation head 1000 has head rotating mechanisms having two axes (S1 and S2). By the operations of these head rotating mechanisms, non-isocentric irradiation can be performed around the rotational axis of the rotary drum 9. Head rotation around the axis S2 must include aiming angle correction corresponding to rotation of the rotary drum 9. However, no aiming angle correction is necessary for head rotation around the axis S1.

The image acquiring X-ray source 97 and sensor array 98 are attached to predetermined portions on the rotary drum 9 so as not to interfere with the irradiation head 1000. These image acquiring X-ray source 97 and sensor array 98 oppose each other. The sensor array 98 is a multi-row type sensor.

(Fourth Embodiment)

Figure 28:
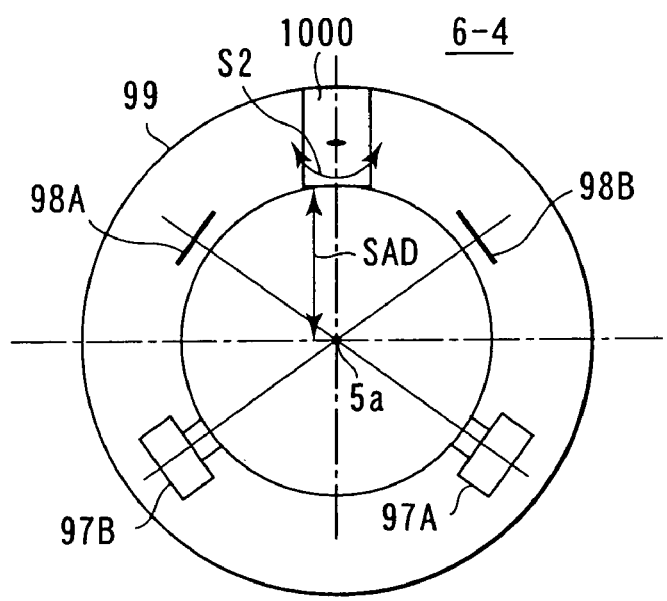
FIG. 28 is a view showing a radiotherapy apparatus according to the fourth embodiment of the present invention in the direction of the bed axis.

A radiotherapy apparatus according to the fourth embodiment of the present invention will be described below with reference to FIG. 28. In FIG. 28, a repetitive explanation of the same portions as in the previous figures will be omitted.

In a radiotherapy apparatus 6-4 of this embodiment, an irradiation head 1000, X-ray sources 97A and 97B, and sensor arrays 98A and 98B are mounted on a rotary drum 99. A set of the X-ray source 97A and sensor array 98A and a set of the X-ray source 97B and sensor array 98B function as X-ray fluoroscopic devices. The viewing lines of these two X-ray fluoroscopic devices are different. Therefore, an X-ray fluoroscopic image containing an image of a landmark or a marker such as a gold microplate in the body of a patient 4 can be acquired in two axial directions. In this way, the movement of the patient's position can be known. As a method of emphasizing an X-ray fluoroscopic image, image processing such as DSA can be performed by using a contrast medium. The irradiation head 1000 is the same as in the third embodiment.

(Fifth Embodiment)

A radiotherapy apparatus according to the fifth embodiment of the present invention will be described below with reference to FIGS. 29 to 37.

Figure 29:
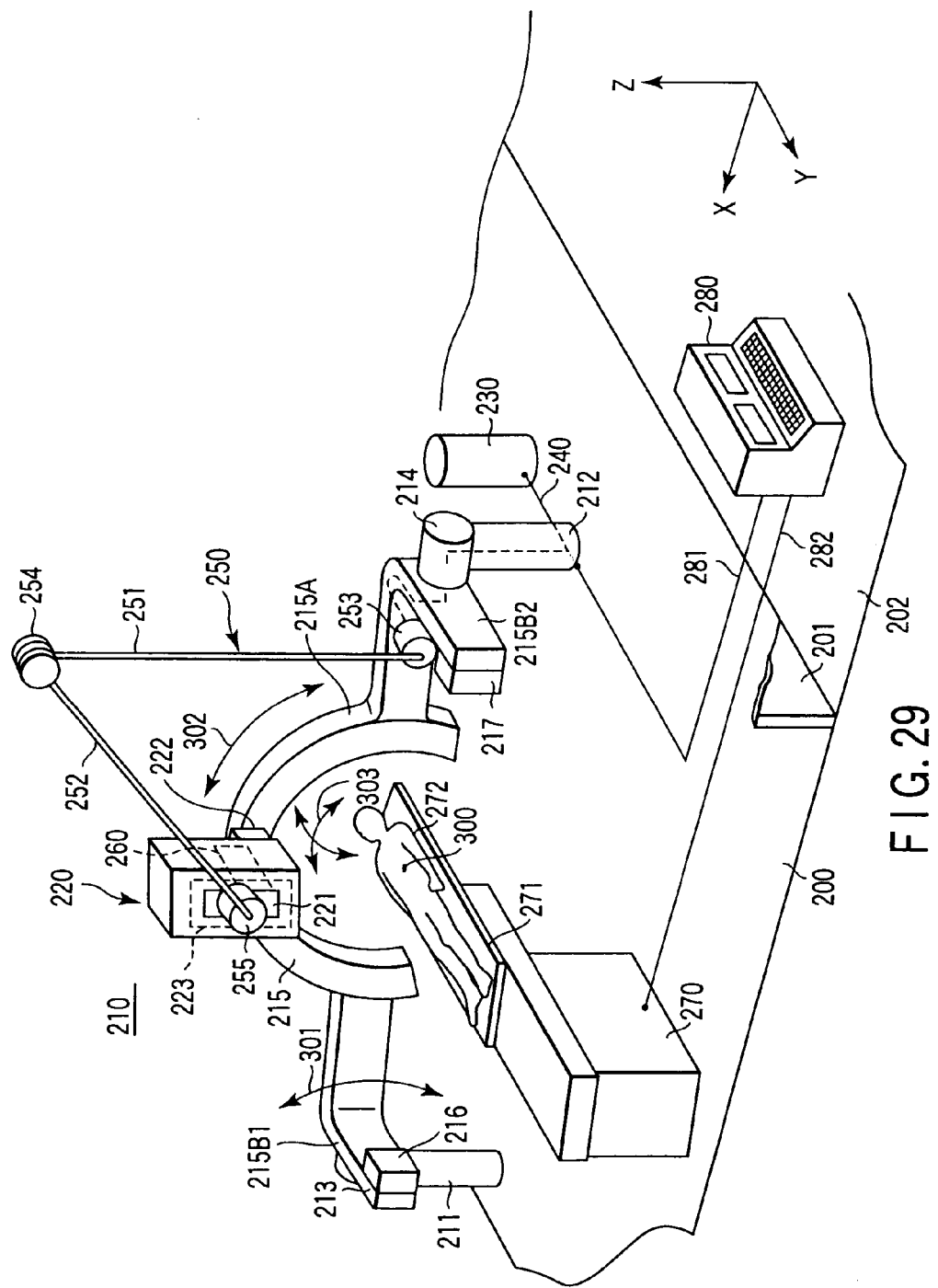
FIG. 29 is a perspective view showing a radiotherapy apparatus according to the fifth embodiment of the present invention.

As shown in FIG. 29, the radiotherapy apparatus of this embodiment comprises elements installed in a therapy room 200, and an element installed in an operation room 202 isolated from the therapy room 200 by a partition 201.

The elements installed in the therapy room 200 are a supporting moving mechanism 210, an irradiation head 220 which is supported and moved on predetermined first spherical coordinates by the supporting moving mechanism 210, a microwave oscillator 230, a fixed waveguide unit 240, moving waveguide unit 250, and intra-head waveguide unit 260 which form a microwave transmission system for transmitting microwave power generated by the microwave oscillator 230 to a therapeutic radiation generator 221 in the irradiation head 220, and a bed 270.

The element installed in the operation room 202 is a system console 280.

The supporting moving mechanism 210 includes a pair of bases 211 and 212 fixed on the floor of the therapy room 200, a pair of tilting mechanisms 213 and 214 formed on the pair of bases 211 and 212, respectively, a guide rail 215 having a semicircular track for supporting and moving the irradiation head 220, and a pair of weights 216 and 217. That is, a track 215A is formed in the middle of the guide rail 215, and two end portions 215B1 and 215B2 of this guide rail 215 are supported by the tilting mechanisms 213 and 214 formed on the bases 211 and 212, respectively. By driving the tilting mechanisms 213 and 214, the guide rail 215 is rotated around an isocenter 300 in a direction indicated by reference numeral 301.

The irradiation head 200 has the therapeutic radiation generator 221 including an electron gun, accelerator, target, collimator, vacuum pump, and the like, a circumferential moving mechanism 222 which circumferentially moves the irradiation head 220 along the track 215A in a direction indicated by reference numeral 302 by a mechanism such as a rack and pinion or a belt and pulley, and a gimbal mechanism 223 which rotates the therapeutic radiation generator 221 in two orthogonal directions indicated by reference numeral 303. The operations of the tilting mechanisms 213 and 214 and circumferential moving mechanism 222 allow isocentric rotation of the irradiation head 220. Also, the operation of the gimbal mechanism 223 (to be described later) permits pseudo non-isocentric rotation of the irradiation head 220.

The microwave oscillator 230 is a microwave electron tube such as a klystron. This microwave oscillator 230, the microwave transmission system, and the therapeutic radiation generator 221 are integrally incorporated into a gantry including an irradiation head as a rotary member in a conventional radiotherapy apparatus such as a small electron linac. However, in the radiotherapy apparatus of this embodiment, a lightweight irradiation head is realized by installing the heavy microwave oscillator 230 on the floor of the therapy room 200. By the combination of this lightweight irradiation head 220 and the characteristic supporting moving mechanism 210, the irradiation head 220 can be moved to an arbitrary position on the spherical coordinate system defined in the space of the therapy room 200.

The moving waveguide unit 250 is a pantograph mechanism including first and second linear waveguides 251 and 252, and first, second, and third rotary couplers 253, 254, and 255. This moving waveguide unit 250 couples the fixed waveguide unit 240 and intra-head waveguide unit 260. That is, of the first, second, and third rotary RF couplers 253, 254, and 255 of the same type, the second rotary RF coupler 254 will be explained as a representative together with the first and second linear waveguides 251 and 252 with reference to FIG. 30.

Figure 30:
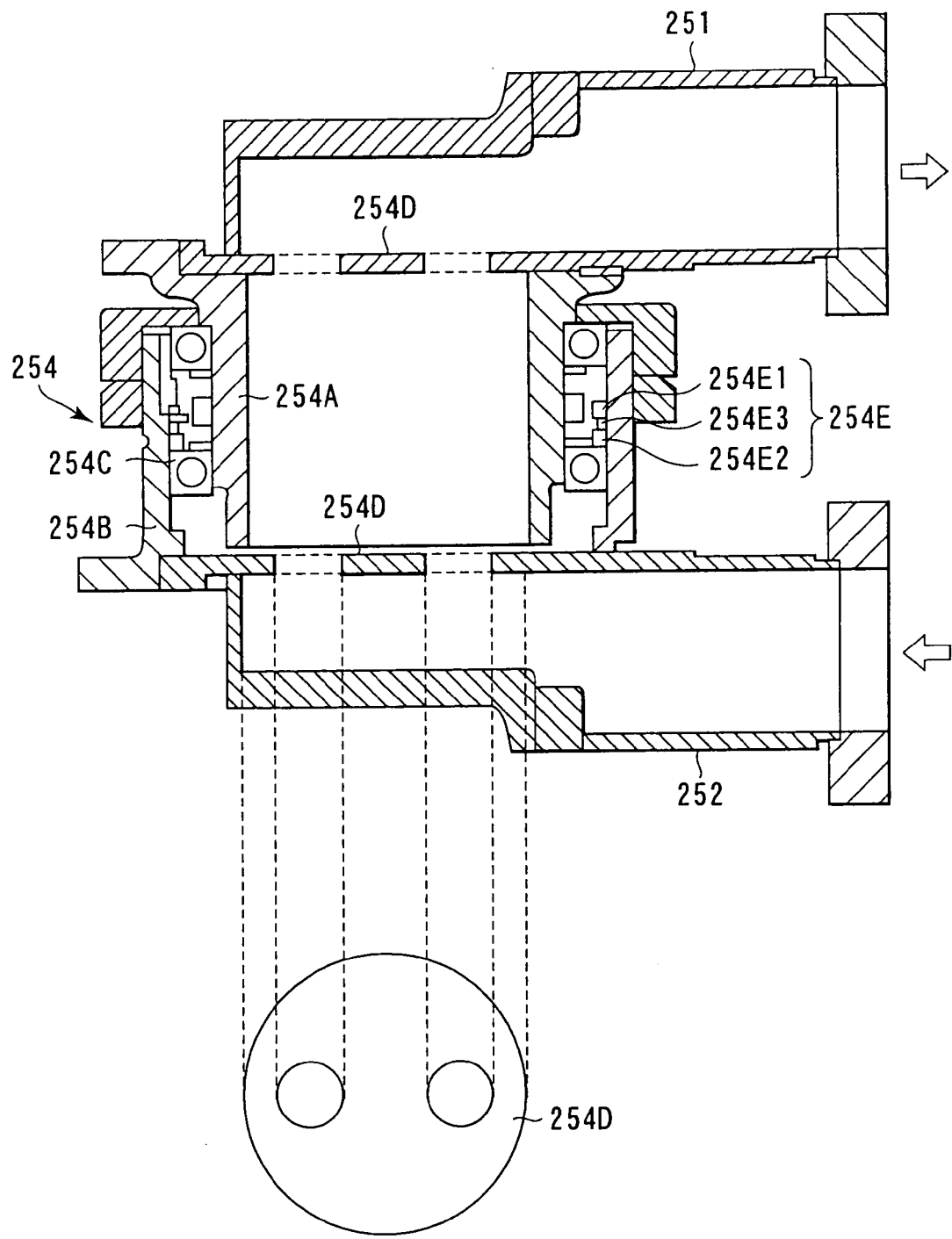
FIG. 30 is a sectional view of a rotary RF coupler of the same embodiment.

Referring to FIG. 30, the second rotary RF coupler 254 includes a first cylindrical member 254A to one end of which the first linear waveguide 251 is connected, and a second cylindrical member 254B which has the same axis as the first cylindrical member 254A, one end of which is rotatably connected to the other end of the first cylindrical member 254A via a bearing 254C, and to the other end of which the second linear waveguide 252 is connected. The axial direction of the first and second cylindrical members 254A and 254B is perpendicular to the extending direction of the first and second linear waveguides 251 and 252.

In the opening of the first and second cylindrical members 254A and 254B, a band filter plate 254D having two holes is formed. In addition, a magnetic sealing mechanism 254E is formed between the first and second cylindrical members 254A and 254B. This magnetic sealing mechanism 254E is used instead of an O-ring for airtight seal, and has a structure in which a magnetic fluid 254E3 is sandwiched between a pair of electromagnets 254E1 and 254E2. This magnetic sealing mechanism 254E formed between the first and second cylindrical members 254A and 254B is more advantageous in maintenance than a conventional O-ring which requires periodic replacement resulting from deterioration.

By the second rotary RF coupler 254 and first and second linear waveguides 251 and 252 as described above, microwave power transmitted in the extending direction of the first linear waveguide 251 is bent at a right angle at the entrance of the second rotary RF coupler 254, bent at a right angle again at its exit, and transmitted in the extending direction of the second linear waveguide 252. Also, the first and second cylindrical members 254A and 254B of the second rotary RF coupler 254 can rotate. Therefore, the first and second linear waveguides 251 and 252 connected at right angles to the first and second cylindrical members 254A and 254B, respectively, can be rotated in different directions.

In the moving waveguide unit 250, therefore, one end of the first linear waveguide 251 having the other end connected to the second rotary RF coupler 254 is connected to the first rotary RF coupler 253 which has the same structure as the second rotary RF coupler 254 and is fixed to the end portion of the guide rail 215, and one end of the second linear waveguide 252 having the other end connected to the second rotary RF coupler 254 is connected to the third rotary RF coupler 255 which has the same structure as the second rotary RF coupler 254 and is fixed to the irradiation head 220. Accordingly, when the irradiation head 220 moves, the first and second cylindrical members 254A and 254B of each of the first, second, and third rotary RF couplers 253, 254, and 255 rotate, so the first and second linear waveguides 251 and 252 can be opened and closed around the second rotary RF coupler 254. This indicates that the moving waveguide unit 250 including the first and second linear waveguides 251 and 252 and the first, second, and third rotary RF couplers 253, 254, and 255 is a pantograph mechanism.

Figure 31:
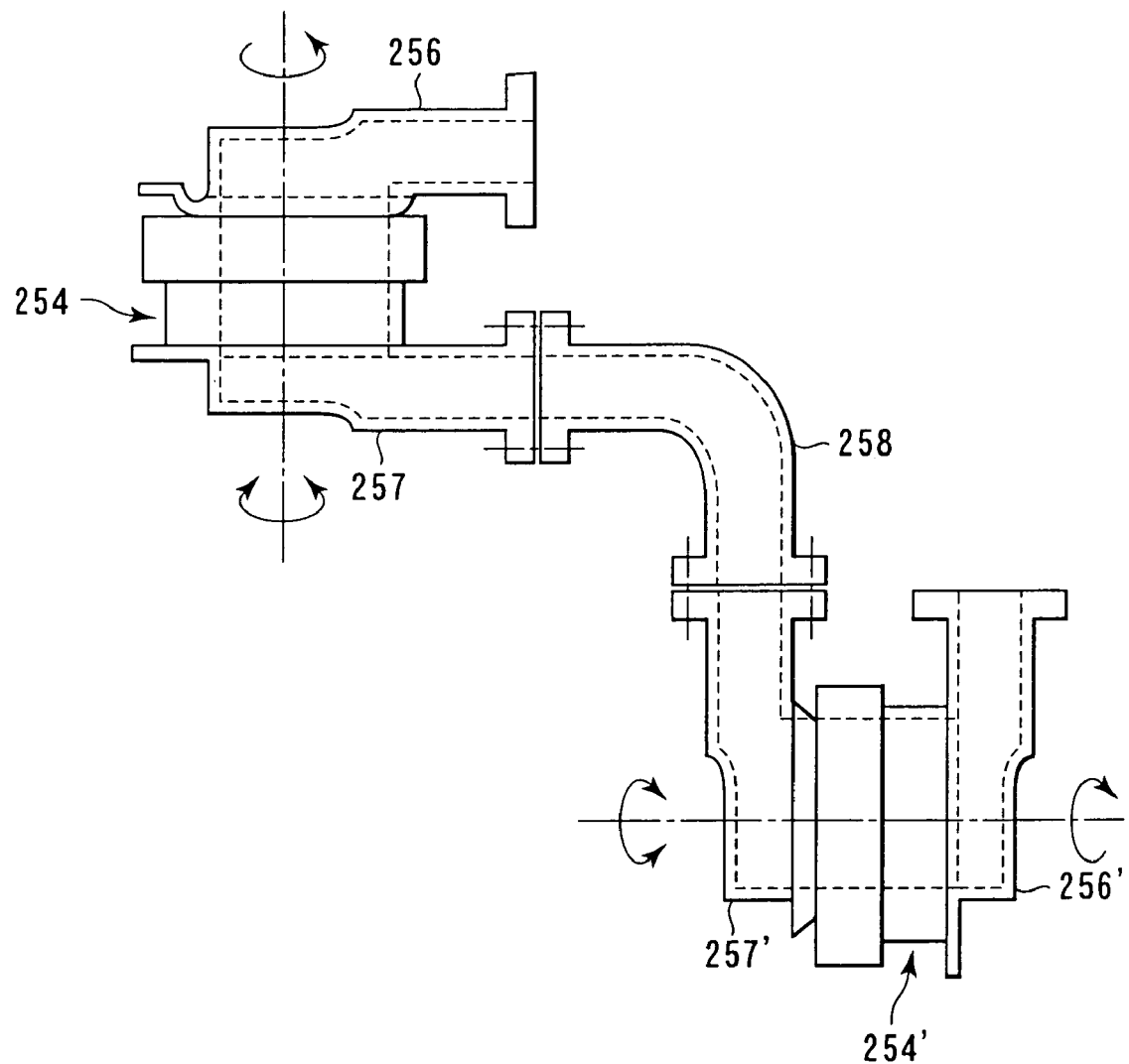
FIG. 31 is a view showing a transmission system combining rotary RF couplers and waveguides in the same embodiment.

FIG. 31 shows an example in which a bent transmission path is formed using two rotary RF couplers 254 and 254' and five waveguides. In this example, the rotary RF coupler 254 and linear waveguides 256 and 257 similar to those shown in FIG. 30 and the rotary RF coupler 254' and linear waveguides 256' and 257' analogous to those described above are coupled by a bent waveguide 258.

As described above, a bent transmission path can be easily formed by manufacturing a plurality of sets of rotary RF couplers 254 shown in FIG. 30 and waveguides, and coupling these sets by bent waveguides.

Figure 32:
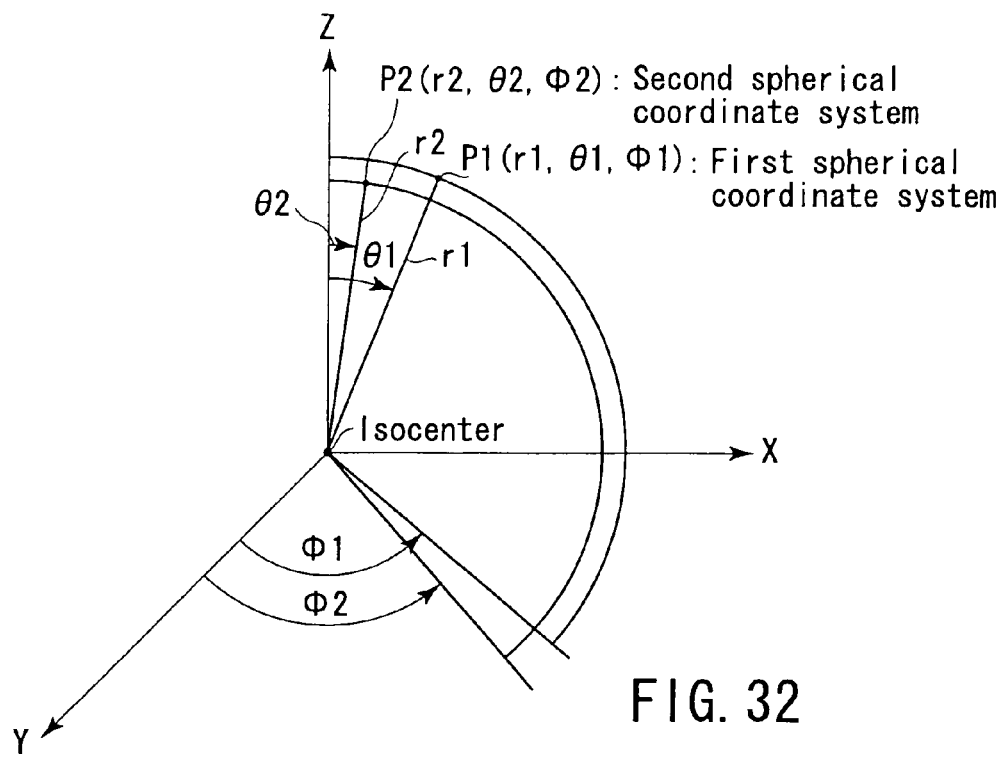
FIG. 32 is a view showing the relationship between a spherical coordinate system pertaining to an irradiation head and a spherical coordinate system pertaining to a moving waveguide unit in the same embodiment.

The relationship between the irradiation head 220 and moving waveguide unit 250 will be explained below with reference to FIG. 32. That is, when the isocenter 300 is defined in FIG. 29, the irradiation head 220 can be moved to a given position on the spherical coordinate system defined in the space of the therapy room 200 by the supporting moving mechanism 210. Referring to FIG. 32, this spherical coordinate system can be indicated by P1(r1, θ1, φ1). r1 is the distance between the isocenter 300 and the target. When the irradiation head 220 moves on this spherical coordinate system P1(r1, θ1, φ1), the third rotary RF coupler 255 of the moving waveguide unit 250 is moved on a spherical coordinate system indicated by P2(r2, θ2, φ2) in relation to the former coordinate system. r2 is the distance between the isocenter 300 and the axis of the third rotary RF coupler 255.

In the radiotherapy apparatus of this embodiment as described above, the moving waveguide unit 250 can be moved on the spherical coordinate system P2 in accordance with the spherical coordinate system P1 on which the irradiation head 220 moves. This makes the movement of the moving waveguide unit 250 follow the movement of the irradiation head 220.

Figures 33, 34:
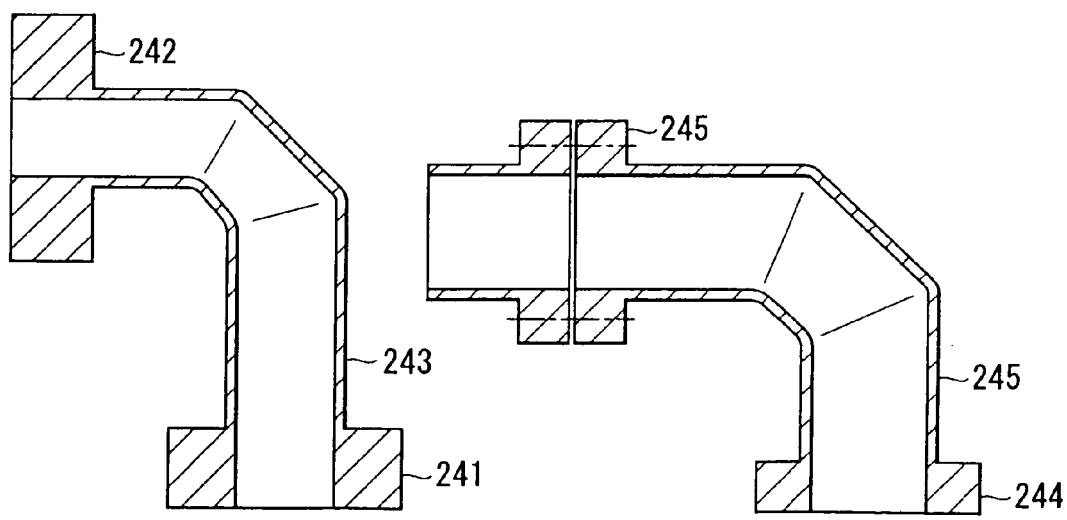
FIG. 33 is a view showing an E-bent waveguide of the same embodiment.
FIG. 34 is a view showing an H-bent waveguide of the same embodiment.
Figure 35:
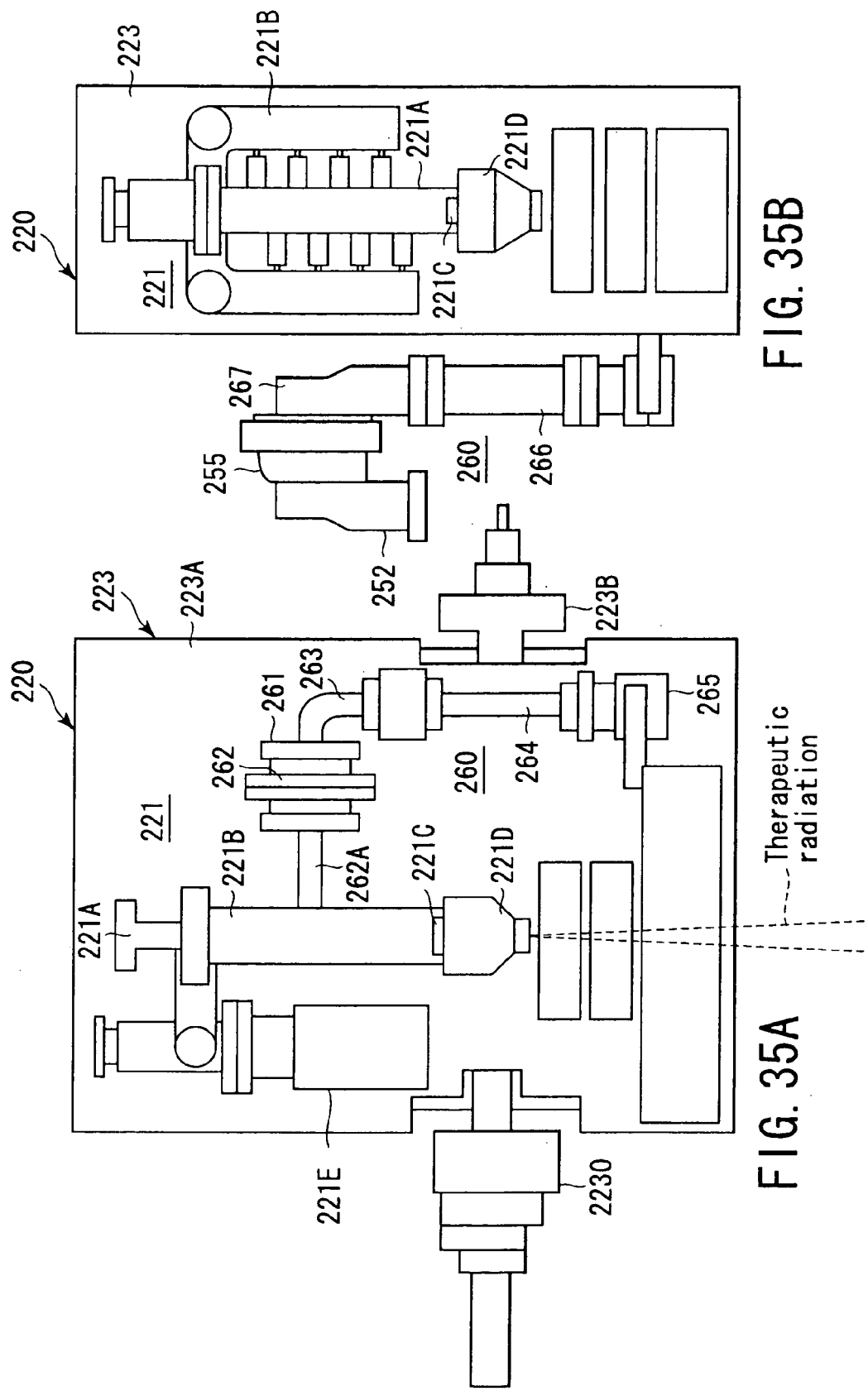
Figure 36:
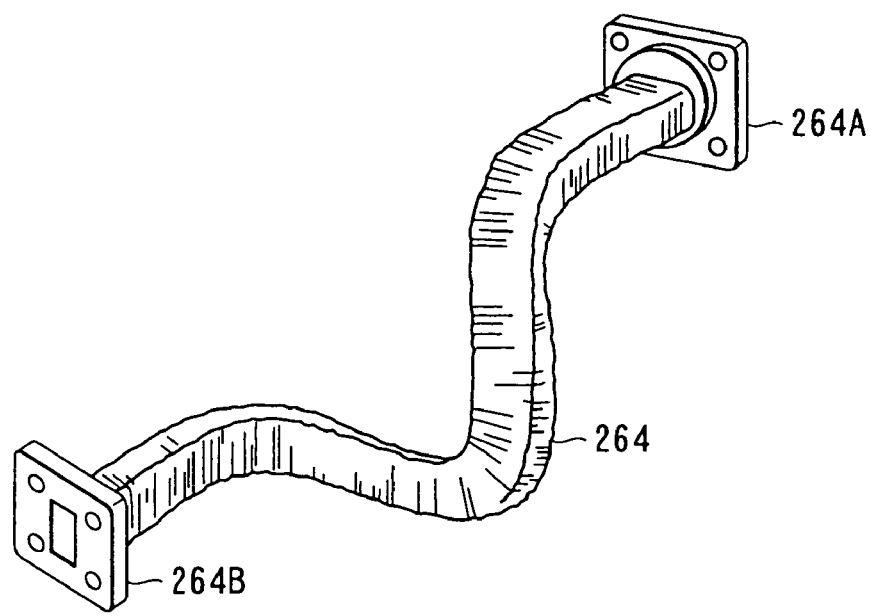
FIG. 36 is a view showing a flexible waveguide of the same embodiment.
Figure 37:
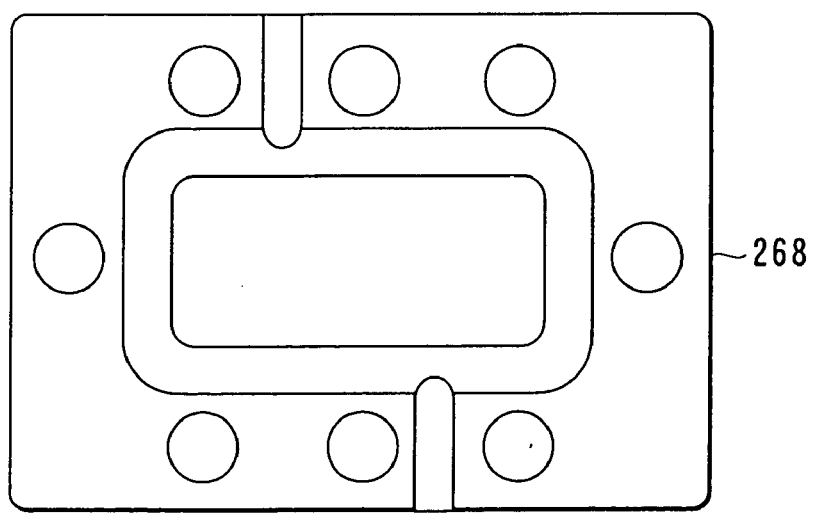
FIG. 37 is a view showing a flange of the same embodiment.

Next, the fixed waveguide unit 240 will be explained. That is, this fixed waveguide unit 240 includes waveguides similar to the linear waveguides used in the moving waveguide unit 250, an E-bent waveguide 243 having flanges 241 and 242 at the two ends as shown in FIG. 33, an H-bent waveguide 245 having flanges 244 and 245 at the two ends as shown in FIG. 34, and rotary RF couplers analogous to the rotary RF couplers 253, 254, and 255 used in the moving waveguide unit 250, and couples the microwave oscillator 230 and the moving waveguide unit 250. Referring to FIG. 29, the fixed waveguide unit 240 is connected from the output end of the microwave oscillator 230 to the first rotary RF coupler 253 formed in the end portion 215B2 of the guide rail 215 through the base 212.

The irradiation head 220 and the intra-head waveguide unit 260 will be described below with reference to FIGS. 35A and 35B. As explained earlier with reference to FIG. 29, the irradiation head 220 has the therapeutic radiation generator 221, circumferential moving mechanism 222, and gimbal mechanism 223, and also includes the intra-head waveguide unit 260. Note that the circumferential moving mechanism 222 is not shown in FIGS. 35A and 35B. Servo mechanisms 223B and 223C for rotating the head in two orthogonal directions are attached to a frame 223A of the gimbal mechanism 223, thereby rotating the whole frame 223A in a position determined by the circumferential moving mechanism. On this frame 223A, an electron gun 221A, an accelerator 221B such as a C-band standing-wave linear accelerator, a target 221C, a collimator 221D, and a vacuum pump 221E coupled with the accelerator 221B are mounted.

In this therapeutic radiation generator 221 as described above, an electron beam emitted from the electron gun 221A is accelerated by the accelerator 221B, and radiation is generated by colliding the accelerated electron beam against the target 221C. This radiation is shaped by the collimator 221D, and the patient (not shown) is irradiated with the therapeutic radiation from the irradiation head 220.

The intra-head waveguide unit 260 is connected to the accelerator 221B in the above arrangement. This intra-head waveguide unit 260 has a rotary RF coupler 261 which incorporates an RF window 262, and one end of which is connected to the accelerator 221B. The other end of this rotary RF coupler 261 is connected to a bent waveguide 263. The rotary RF coupler 261 incorporating the RF window 262 and the bent waveguide 263 are mounted on the frame 223A of the gimbal mechanism 223. The circumferential moving mechanism has waveguides 265, 266, and 267, and the waveguide 267 is connected to the third rotary RF coupler 255 of the moving waveguide unit 250. The bent waveguide 263 mounted on the frame 223A of the gimbal mechanism 223 and the waveguide 265 of the circumferential moving mechanism are coupled by a flexible waveguide 264 having flanges 264A and 264B illustrated in detail in FIG. 36. Note that a flange 268 shown in FIG. 37 can be used as the flanges shown in FIGS. 33, 34, and 36. If a bent transmission path is to be formed in the intra-head waveguide unit 260, it is possible to use the E-bent waveguide 243 having the flanges 241 and 242 at the two ends shown in FIG. 33, and the H-bent waveguide 245 having the flanges 244 and 245 at the two ends shown in FIG. 34.

The bed 270 shown in FIG. 29 has a top plate 271 which moves in at least one of the Z direction (vertical direction) and X and Y directions (horizontal directions) while a patient 272 is placed on this top plate 271. The top plate 271 is moved by a moving mechanism (not shown) of the bed 270.

The system console 280 shown in FIG. 29 automatically or manually controls the tilting mechanisms 213 and 214, the therapeutic radiation generator 221, circumferential moving mechanism 222, and gimbal mechanism 223 of the irradiation head 220, the microwave oscillator 230, and the bed 270.

The radiotherapy apparatus of this embodiment constructed as above has the following effects. That is, the lightweight irradiation head 220 is realized by installing the heavy microwave oscillator 230 on the floor of the therapy room 200. Also, the combination of this irradiation head 220 and the characteristic supporting moving mechanism 210 permits the irradiation head 220 to move to an arbitrary position on the spherical coordinate system P1 defined in the space of the therapy room 200.

Additionally, in the radiotherapy apparatus of this embodiment, the moving waveguide unit 250 can be moved on the spherical coordinate system P2 in accordance with the spherical coordinate system P1 on which the irradiation head 220 moves. This makes the movement of the moving waveguide unit 250 follow the movement of the irradiation head 220. Accordingly, microwave power can be easily supplied to the irradiation head 220 in a given position.

Furthermore, the moving waveguide unit 250 forms a pantograph mechanism by the first and second linear waveguides 251 and 252, and the first, second, and third rotary RF couplers 253, 254, and 255. Therefore, the first and second linear waveguides 251 and 252 can be readily opened and closed around the second rotary RF coupler 254, and the moving amount can be absorbed. This makes it possible to prevent interference with the patient 272.

Also, the fixed waveguide unit 240 and intra-head waveguide unit 260 are formed using the E-bent waveguide 243, the H-bent waveguide 245, and rotary RF couplers similar to the rotary RF couplers 253, 254, and 255, in addition to linear waveguides. Hence, a bent transmission path can be formed in the minimum distance. This contributes to downsizing.

The magnetic sealing mechanism 254E is formed between the first and second cylindrical members 254A and 254B of the rotary RF coupler 254. Accordingly, the generation of leaks caused by wear can be suppressed compared to the conventional O-ring, and the cycle of replacement by deterioration can be extended.

In addition, the bent waveguide 263 mounted on the gimbal mechanism 223 of the intra-head waveguide unit 260 is coupled with the waveguide 265 of the circumferential moving mechanism by the flexible waveguide 264. Therefore, even when the therapeutic radiation generator 221 including the bent waveguide 263 causes a slight angular displacement by head rotation by the gimbal mechanism 223, this positional deviation of the therapeutic radiation generator 221 caused by the head rotation can be easily absorbed by the flexible waveguide 264. This allows smooth pseudo non-isocentric rotation of the irradiation head 220 by the gimbal mechanism 223, while predetermined microwave power is supplied to the therapeutic radiation generator 221.

(Sixth Embodiment)

Figure 38:
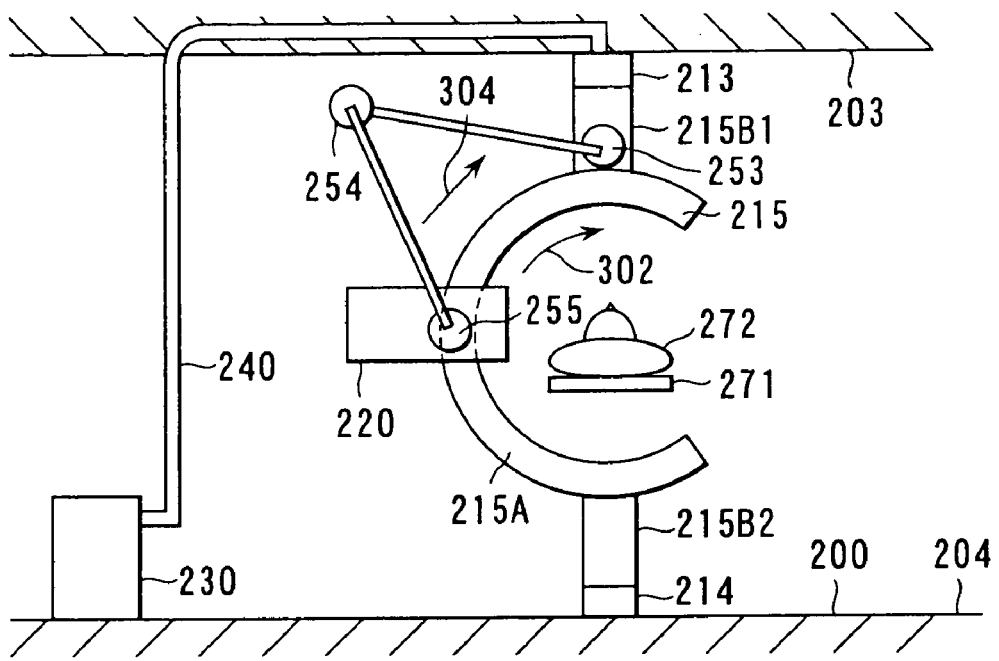
FIG. 38 is a perspective view showing a radiotherapy apparatus according to the sixth embodiment of the present invention.
Figure 39:
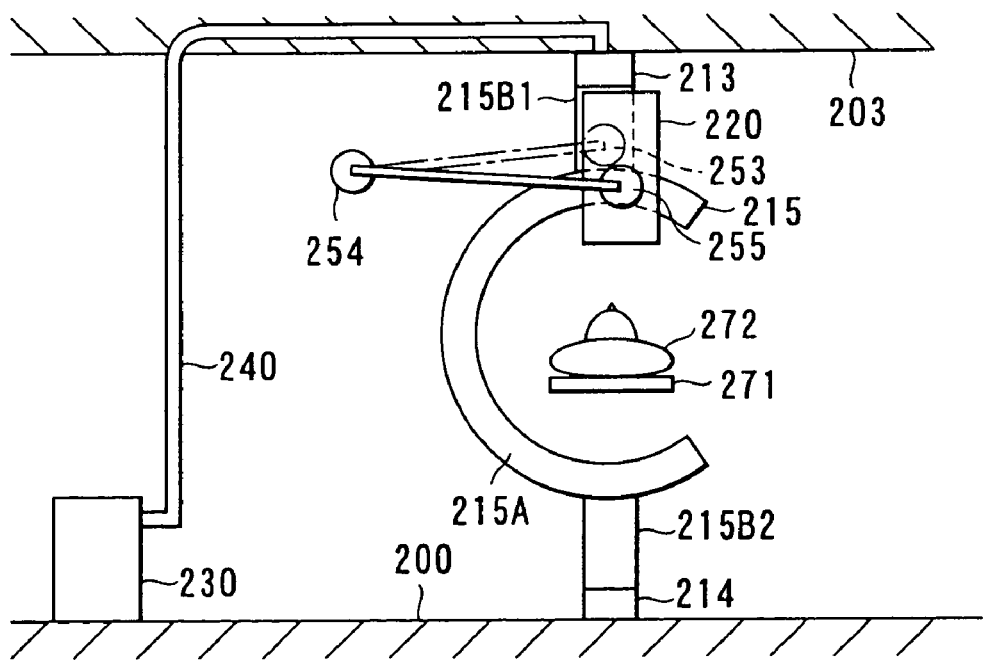
FIG. 39 is a view showing the operation of a moving waveguide unit of the radiotherapy apparatus according to the same embodiment.

A radiotherapy apparatus according to the sixth embodiment of the present invention will be described below with reference to FIGS. 38 and 39. In FIGS. 38 and 39, the same reference numerals as in FIGS. 29 to 37 denote the same parts, and an explanation thereof will be omitted.

To further utilize the pantograph mechanism of a moving waveguide unit 250, this radiotherapy apparatus according to the sixth embodiment has an arrangement in which a pair of tilting mechanisms 213 and 214 of a supporting moving mechanism 210 are arranged on a ceiling 203 and floor 204 of a therapy room 200.

With this arrangement, the same functions and effects as the radiotherapy apparatus according to the fifth embodiment are achieved. In addition, first and second linear waveguides 251 and 252 of the moving waveguide unit 250 are opened and closed between the ceiling 203 and floor 204. Therefore, an irradiation head 220 can be retracted from a patient 272 toward the ceiling 203. This reduces interference with and a sense of oppression on the patient. In this arrangement, a fixed waveguide unit 240 can be arranged along the ceiling 203 and a wall or embedded in the ceiling 203 and the wall. This makes it possible to further utilize the therapy room 200 for therapy, and prevent collisions against doctors, technicians, and nurses. This also improves the therapeutic efficiency.

In the radiotherapy apparatuses of the fifth and sixth embodiments, image acquiring apparatuses, such as an X-ray CT apparatus or MRI apparatus in the first to fourth embodiments can be combined, and the irradiation field can be positioned by an acquired diseased part image as in the first to fourth embodiments. In this case, the radiotherapy apparatus and the image acquiring apparatus can be interlocked by the console 280.

As described above, the present invention can provide a radiotherapy apparatus having high therapeutic performance.

What is claimed is:

1. A radiotherapy apparatus comprising:
    an irradiation head having a linear accelerator and an intra-head waveguide unit whose one end portion is electromagnetically connected to the linear accelerator;
    a supporting moving mechanism which supports and moves the irradiation head on predetermined first spherical coordinates;
    a microwave oscillator which generates microwaves to be supplied to the irradiation head, and which is placed in a stationary position;
    a fixed waveguide unit having one end portion electromagnetically connected to the microwave oscillator, and the other end portion positioned on the supporting moving mechanism; and
    a moving waveguide unit having one end portion electromagnetically connected to the other end portion of the fixed waveguide unit positioned on the supporting moving mechanism, and the other end portion electromagnetically connected to the other end portion of the intra-head waveguide unit.

2. A radiotherapy apparatus according to claim 1, wherein the moving waveguide unit comprises means which moves on second spherical coordinates related to the first spherical coordinates.

3. A radiotherapy apparatus according to claim 1, wherein the intra-head waveguide unit, fixed waveguide unit, and moving waveguide unit include a waveguide and rotary RF coupler.

4. A radiotherapy apparatus according to claim 1, wherein the moving waveguide unit comprises a pantograph mechanism including a waveguide and rotary RF coupler which open and close in accordance with the movement of the irradiation head.

5. A radiotherapy apparatus according to claim 4, wherein the pantograph mechanism comprises means which closes in a direction away from a patient to be irradiated with therapeutic radiation from the irradiation head.

6. A radiotherapy apparatus according to claim 5, wherein the fixed waveguide unit is installed along the ceiling and wall of a therapy room.

7. A radiotherapy apparatus according to claim 1, wherein at least one of the intra-head waveguide unit and fixed waveguide unit includes a bent waveguide.

8. A radiotherapy apparatus according to claim 1, wherein at least one of the intra-head waveguide unit and fixed waveguide unit includes a flexible waveguide.

9. A radiotherapy apparatus according to claim 3, wherein the rotary RF coupler includes a first cylindrical member having one end to which a waveguide is connected, and a second cylindrical member which has the same axis as the first cylindrical member, one end of which is rotatably connected to the other end of the first cylindrical member, and to the other end of which another waveguide is connected.

10. A radiotherapy apparatus according to claim 3, wherein the rotary RF coupler includes a magnetic seal which seals at least one of an internal vacuum and sealed gas.

11. A radiotherapy apparatus according to claim 1, wherein the irradiation head comprises a gimbal mechanism which rotates the irradiation head in at least two orthogonal directions.

12. A radiotherapy apparatus according to claim 1, further comprising:

an isocentric rotating mechanism which rotates the irradiation head around an isocenter; and a pseudo non-isocentric rotating mechanism which rotates the irradiation head in a position where the irradiation head is rotated a predetermined angle by the isocentric rotating mechanism.

* * * * *

UNITED STATES PATENT AND TRADEMARK OFFICE
CERTIFICATE OF CORRECTION

PATENT NO. : 6,977,987 B2 Page 1 of 1
APPLICATION NO. : 10/762358
DATED : December 20, 2005
INVENTOR(S) : Yamashita et al.

It is certified that error appears in the above-identified patent and that said Letters Patent is hereby corrected as shown below:

On the Cover Page;
Insert item -- (30)   Foreign Application Priority Data
            August 24, 2001    (JP) ................2001-254891
            August 24, 2001    (JP) ................2001-254892 --

Signed and Sealed this

Twenty-ninth Day of August, 2006

JON W. DUDAS
*Director of the United States Patent and Trademark Office*